(12) United States Patent
Panetta et al.

(10) Patent No.: US 7,722,634 B2
(45) Date of Patent: May 25, 2010

(54) MEDICAL DEVICE AND METHOD OF INTRAVENOUS FILTRATION

(75) Inventors: Carmelo J. Panetta, St. Paul, MN (US); Robert F. Wilson, Roseville, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 1222 days.

(21) Appl. No.: 10/884,600

(22) Filed: Jul. 2, 2004

(65) Prior Publication Data

US 2005/0038468 A1 Feb. 17, 2005

Related U.S. Application Data

(60) Provisional application No. 60/484,717, filed on Jul. 3, 2003.

(51) Int. Cl.
*A61M 29/00* (2006.01)
(52) U.S. Cl. .................. 606/200; 606/194; 623/1.11
(58) Field of Classification Search ............. 606/191, 606/192, 194, 200, 195; 623/1.11
See application file for complete search history.

(56) References Cited

U.S. PATENT DOCUMENTS

| | | | |
|---|---|---|---|
| 4,723,549 A * | 2/1988 | Wholey et al. ............ 606/194 |
| 5,498,657 A | 3/1996 | Sugiyama et al. | |
| 5,769,816 A | 6/1998 | Barbut et al. | |
| 5,848,964 A | 12/1998 | Samuels | |
| 5,954,745 A | 9/1999 | Gertler et al. | |
| 5,972,019 A * | 10/1999 | Engelson et al. ............ 606/200 |
| 5,989,281 A | 11/1999 | Barbut et al. | |
| 6,086,605 A | 7/2000 | Barbut et al. | |
| 6,090,097 A | 7/2000 | Barbut et al. | |
| 6,117,154 A | 9/2000 | Barbut et al. | |
| 6,136,016 A | 10/2000 | Barbut et al. | |
| 6,142,987 A | 11/2000 | Tsugita | |
| 6,231,544 B1 | 5/2001 | Tsugita et al. | |
| 6,235,045 B1 | 5/2001 | Barbut et al. | |
| 6,280,413 B1 | 8/2001 | Clark et al. | |

(Continued)

OTHER PUBLICATIONS

Fasseas et al., "Distal Protection Devices During Percutaneous Coronary and Carotid Interventions," *Current Controlled Trials in Cardiovascular Medicine*, Dec. 2001, vol. 2 No. 6, 6 pgs.

(Continued)

*Primary Examiner*—Todd E Manahan
*Assistant Examiner*—Jennifer L Hornberger
(74) *Attorney, Agent, or Firm*—Mueting Raasch & Gebhardt, P.A.

(57) ABSTRACT

A medical catheter having an elongate body, a first expandable balloon and a filter assembly. The filter assembly includes an expandable filter having a first portion coupled to a portion of the medical catheter and a second portion positioned around at least a portion of the first expandable balloon to form a channel between the filter assembly and the first expandable balloon. The filter assembly can further include struts coupled to the second portion of the expandable filter, where the struts tether the second portion of the expandable filter to the elongate body adjacent the proximal end of the first expandable balloon. The first expandable balloon can be used in procedures to dilate blood vessels, including those that deploy stents, where the expandable filter assembly captures particles, including embolic particles, from the blood during the procedure.

57 Claims, 15 Drawing Sheets

U.S. PATENT DOCUMENTS

| | | | |
|---|---|---|---|
| 6,290,710 B1 * | 9/2001 | Cryer et al. | 606/200 |
| 6,340,364 B2 * | 1/2002 | Kanesaka | 606/200 |
| 6,371,970 B1 | 4/2002 | Khosravi et al. | |
| 6,423,086 B1 | 7/2002 | Barbut et al. | |
| 6,485,500 B1 * | 11/2002 | Kokish et al. | 606/194 |
| 6,511,496 B1 * | 1/2003 | Huter et al. | 606/200 |
| 6,716,237 B1 * | 4/2004 | Alt | 623/1.11 |
| 6,746,469 B2 * | 6/2004 | Mouw | 606/200 |
| 6,761,732 B2 * | 7/2004 | Burkett et al. | 623/1.11 |
| 2001/0020175 A1 * | 9/2001 | Yassour et al. | 606/200 |
| 2002/0169474 A1 | 11/2002 | Kusleika et al. | |
| 2003/0176886 A1 * | 9/2003 | Wholey et al. | 606/200 |

OTHER PUBLICATIONS

Stone et al., "Distal Filter Protection During Saphenous Vein Graft Stenting: Technical and Clinical Correlates of Efficacy," *Journ. of Amer. College of Cardiology*, vol. 40, No. 10. (2002) pp. 1882-1888i.

* cited by examiner

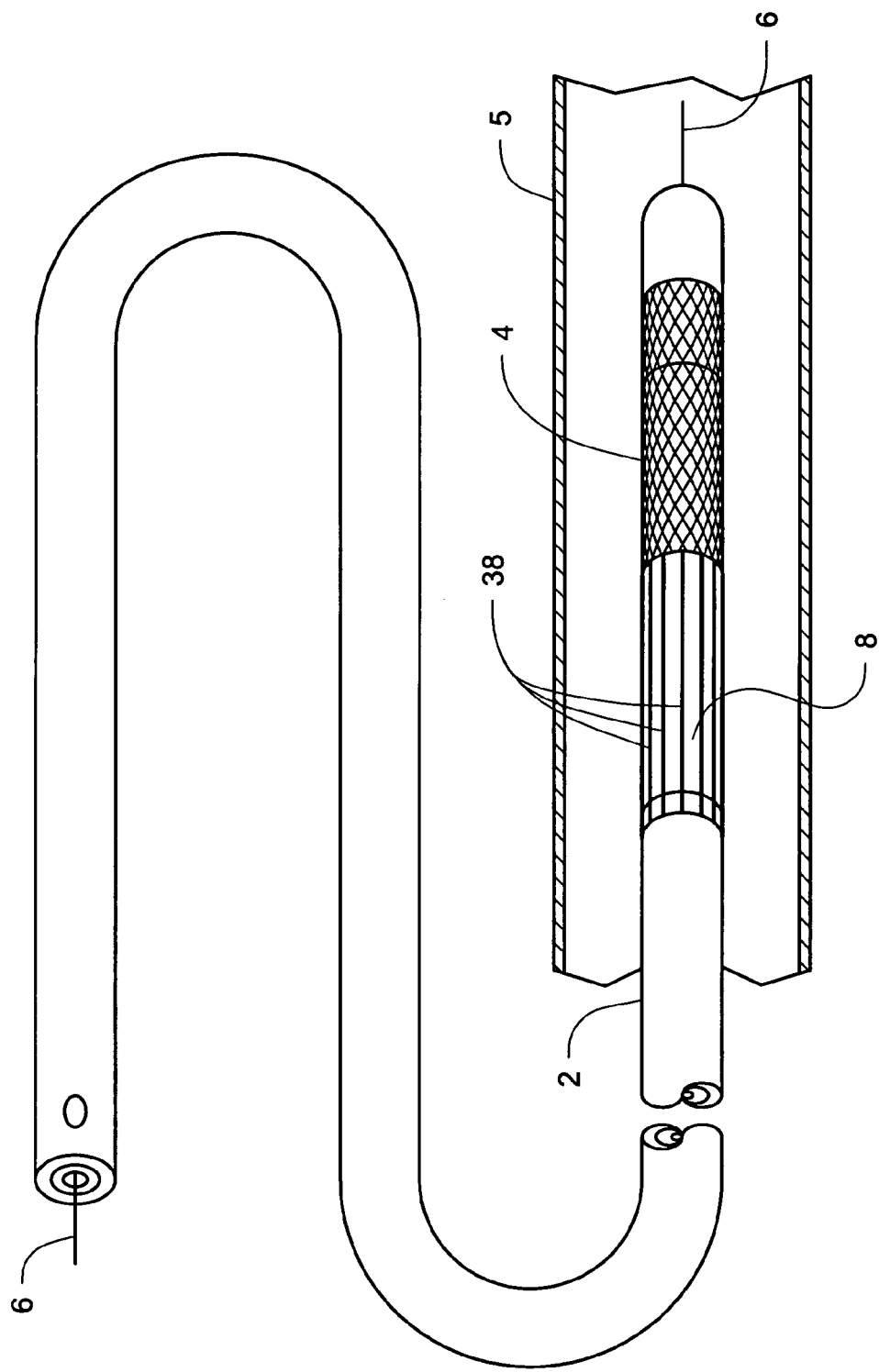

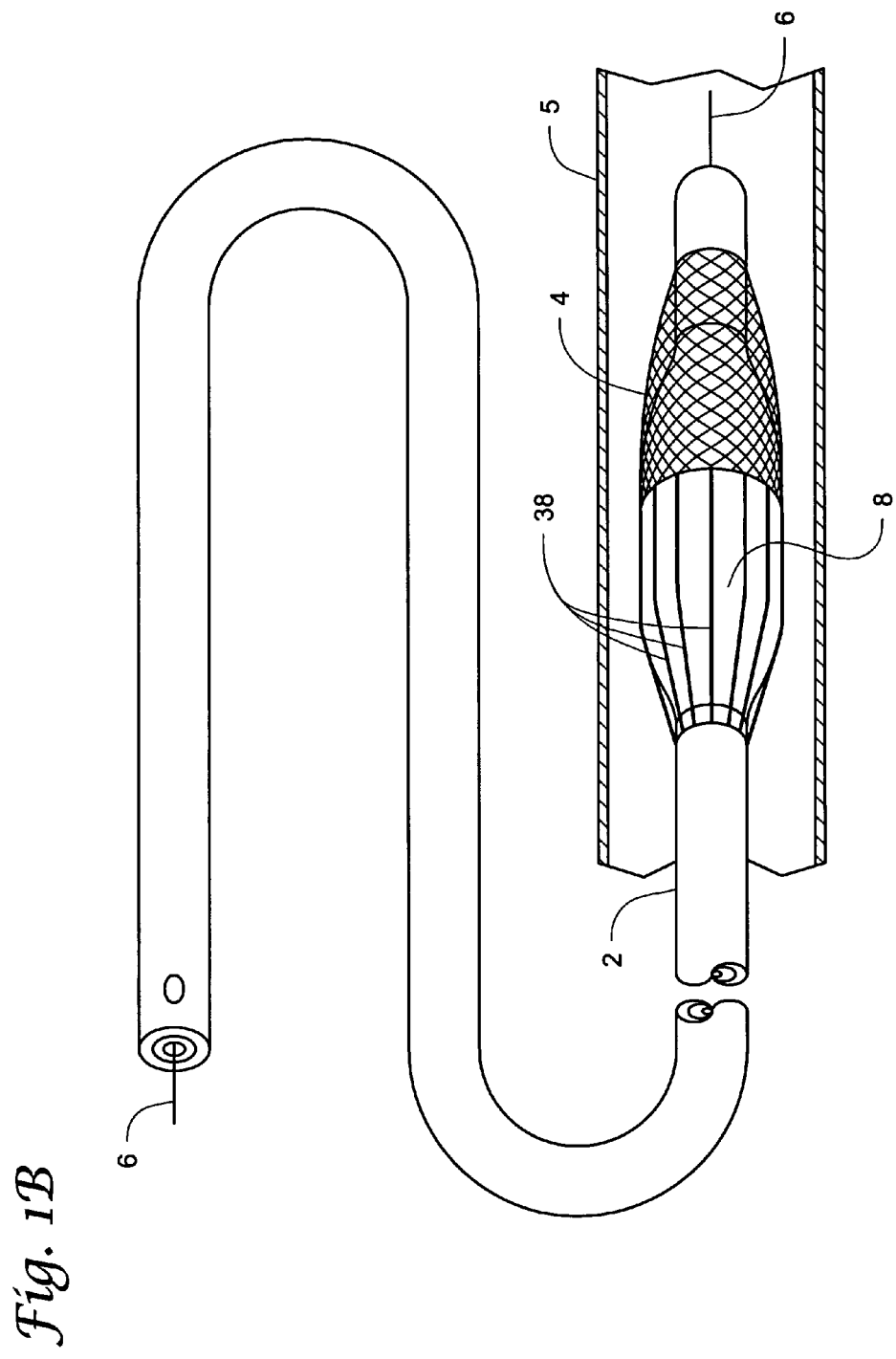

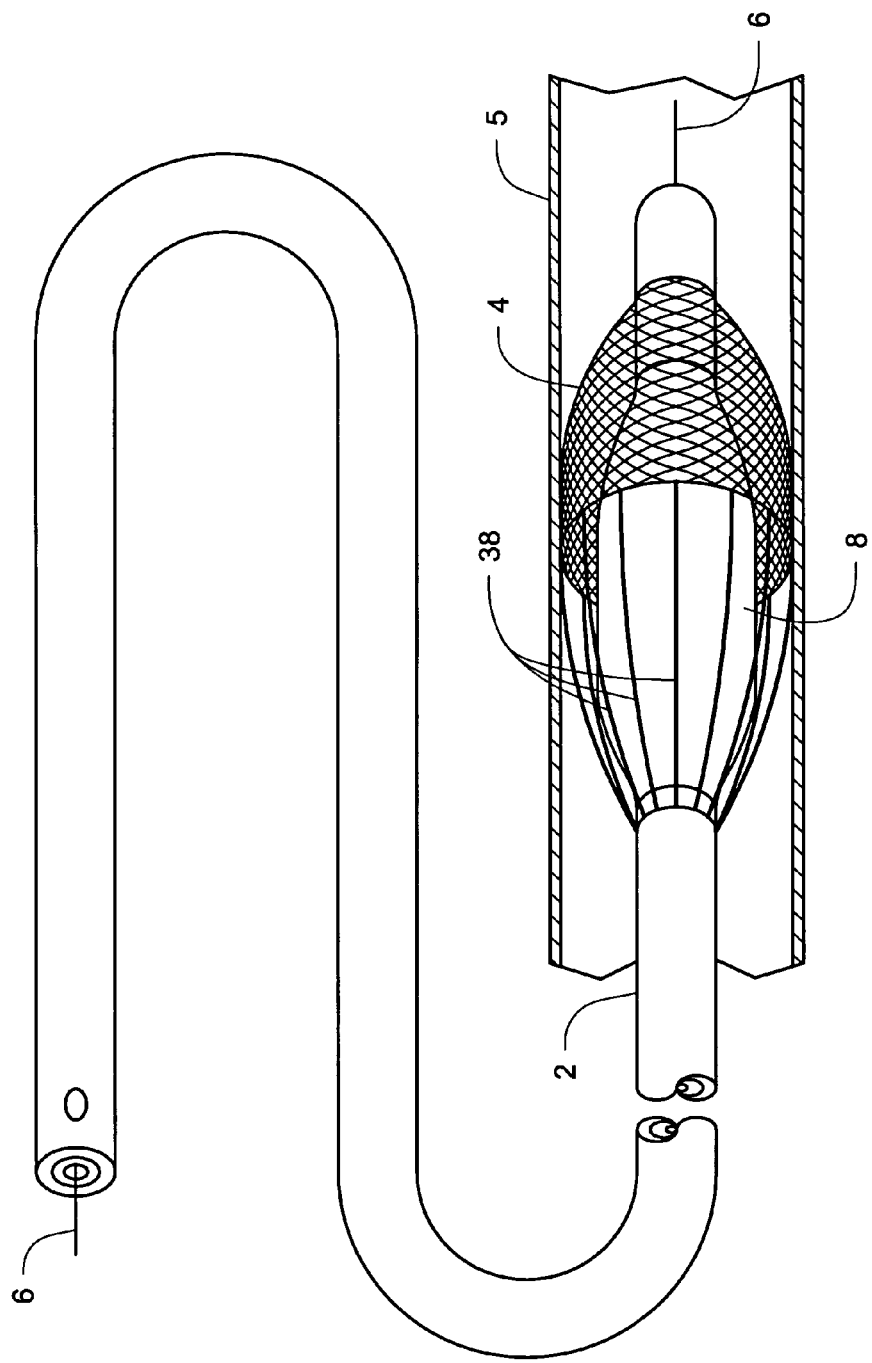

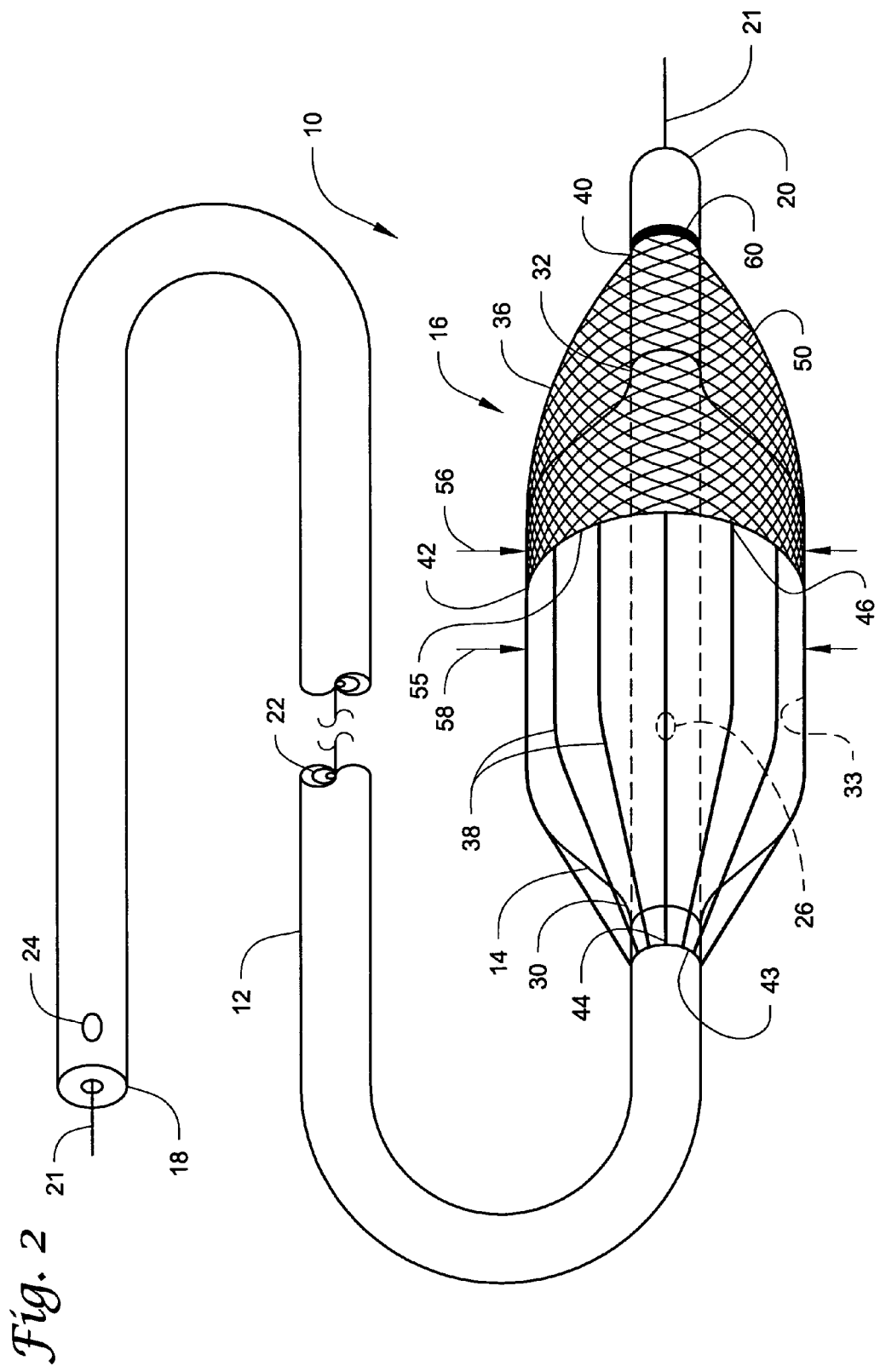

MEDICAL DEVICE AND METHOD OF INTRAVENOUS FILTRATION

This application claims the benefit of U.S. Provisional Application Ser. No. 60/484,717, filed Jul. 3, 2003, which is incorporated herein by reference in its entirety.

TECHNICAL FIELD

The present invention relates generally to medical device catheters and methods of their use.

BACKGROUND

Percutaneous transluminal devices have been successfully used in treating thrombotic or atherosclerotic lesions in blood vessels. These devices include those for directional atherectomy and coronary angioplasty with or without stent deployment. In addition to being used in angioplasty, stenting, and/or atherectomy in the tubular conduits (e.g., blood vessels), percutaneous transluminal devices have also been used in treating other vascular lesions associated with, for example, carotid artery stenosis, arterial occlusive disease (especially the aorta, the iliac artery, and the femoral artery), renal artery stenosis caused by atherosclerosis or fibromuscular disease, superior vena cava syndrome, and occlusive iliac vein thrombosis resistant to thrombolysis.

One complication common to use of percutaneous transluminal devices is the dislodgment of embolic particles that occur during the treatment of the lesion in the blood vessel. This dislodgement of embolic particles has the potential of occluding downstream vessels leading to ischemic (e.g., stroke) or infarct event occurring in the organ having the occluded vessel(s). These embolic particles include calcium, intimal debris, atheromatous plaque, and/or thrombi.

Presently, there is a need in the art to address dislodged embolic particles that occur during percutaneous transluminal procedures. While a variety of approaches have been suggested and/or attempted, the need for a percutaneous transluminal device to address the problem of dislodged embolic particles during the treatment of lesions in blood vessels still exists.

SUMMARY OF THE INVENTION

The present invention provides a medical catheter, including a medical system, and method of using the medical catheter for addressing the problem of dislodged embolic particles during the treatment of lesions in blood vessels still exits.

The present invention includes an apparatus and/or system for use in surgery that includes one or more features described herein. The apparatus and/or system of the present invention includes a medical catheter. The medical catheter has an elongate body that includes at least a first lumen extending between an inlet port and an outlet port in the elongate body. The medical catheter further includes a first expandable balloon having a proximal end and a distal end, where the proximal end and the distal end are coupled to the elongate body. The outlet port can be positioned between the proximal end and the distal end so as to be in fluid communication with the first expandable balloon.

The medical catheter further includes a filter assembly. The filter assembly includes an expandable filter and a plurality of struts, where the expandable filter includes a first portion coupled to a portion of the medical catheter and a second portion coupled to the plurality of struts. In the present example, the struts tether the second portion of the expandable filter to the elongate body adjacent the proximal end of the first expandable balloon. The struts of the present invention can be constructed of any number of materials and take any number of forms, including, but not limited to, cables, mesh, and/or wire.

The expandable filter can be positioned over at least a portion of both the elongate body and the distal end of the first expandable balloon, where the inflating first expandable balloon can be used to deploy the expandable filter. In addition, the second portion of the expandable filter comprises a lip defining an opening into a volume defined by the expandable filter, where the lip moves along an outer surface of the first expandable balloon as the first expandable balloon inflates. In one embodiment, the lip of the expandable filter comprises a diameter no larger than about a diameter of the first expandable balloon.

The medical catheter of the present invention can further include a collar positioned around the elongate body adjacent the proximal end of the first expandable balloon, where the plurality of struts can be coupled to the collar. The collar further includes a retracting mechanism to move the collar longitudinally along the elongate body. Moving the collar along the elongate body allows for at the expandable filter to be closed over at least a portion of the first expandable balloon.

In an alternative embodiment, the elongate body includes a second lumen extending from a proximal end of the elongate body to a plurality of surfaces that define openings through the elongate body adjacent the proximal end of the first expandable balloon. The plurality of struts can be coupled to a retracting wire in the second lumen through the plurality of surfaces that define the openings. The retracting wire can then be moved to pull the plurality of struts longitudinally along the elongate body so as to draw the expandable filter over and into contact with at least a portion of the first expandable balloon.

The medical catheter of the present invention can further include radial support arms coupled to first portion and the second portion of the expandable filter that can help in providing a predetermined shape to the expandable filter. In addition, the medical catheter can also include a vascular stent positioned over at least a portion of the first expandable balloon and/or positioned over at least a portion of the filter assembly and the first expandable balloon.

In an additional embodiment, the medical catheter can further include a second expandable balloon coupled to the elongate body that can be spaced apart from the first expandable balloon. The first lumen of the elongate body of the medical catheter also further includes a second outlet port in the elongate body, where the second outlet portion is in fluid communication with the second expandable balloon.

The medical catheter of the present invention can include a first expandable balloon that will be encased by a sleave having holes or gaps that allow particles to be captured after balloon deflation. The sleave can be over the balloon or distal to the balloon, wherein a distal portion of the sleave does not have holes to allow for capture of particles before embolization downstream.

The medical device system of the present invention can include the medical catheter described herein in addition to an inflation device that includes a fluid output port to couple to the inlet port of the first lumen. The inflation device further includes a fluid pressure generator coupled to the fluid output port to deliver pressurized fluid through the fluid output port to the first expandable balloon.

In an additional embodiment, the medical catheter of the present invention can include an elongate body having at least a first lumen extending between an inlet port and an outlet port in the elongate body; a first expandable balloon that includes a proximal end and a distal end, where the proximal end and the distal end are coupled to the elongate body, and where the outlet port is positioned between the proximal end and the distal end so as to be in fluid communication with the first expandable balloon; and a filter assembly that includes an expandable filter, where the expandable filter comprises a first portion coupled to a portion of the medical catheter and a second portion positioned around at least a portion of the first expandable balloon to form a channel between the filter assembly and the first expandable balloon.

The channel can be formed by the first expandable balloon and the expandable filter. In one embodiment, the first expandable balloon includes an outer surface and the expandable filter includes an inner surface, where the outer surface and the inner surface form the channel between the filter assembly and the first expandable balloon. In one example, the outer surface of the first expandable balloon includes concave regions and convex regions, where the concave regions and the convex regions and the expandable filter form the channel.

In addition, the second portion of the expandable filter can include an elastic element that is stretched when the first expandable balloon expands as it inflates, and contracts when the first expandable balloon is deflated. The filter assembly can further include a plurality of struts, as described herein, coupled to the second portion of the expandable filter, where the struts tether the second portion of the expandable filter to the elongate body adjacent the proximal end of the first expandable balloon.

The expandable filter can be positioned over at least a portion of both the elongate body and the distal end of the first expandable balloon, where the inflating first expandable balloon can be used to deploy the expandable filter. In addition, the second portion of the expandable filter comprises a lip defining an opening into a volume of the channel formed by the expandable filter, where the lip moves along an outer surface of the first expandable balloon as the first expandable balloon inflates. In one embodiment, the lip includes an elastic element that is stretched when the first expandable balloon expands. In addition, the lip of the expandable filter can have a diameter no larger than about a diameter of the first expandable balloon.

The medical catheter of the present invention can further include a collar positioned around the elongate body adjacent the proximal end of the first expandable balloon, where the plurality of struts can be coupled to the collar. The collar further includes a retracting mechanism to move the collar longitudinally along the elongate body. Moving the collar along the elongate body allows for at the expandable filter to be closed over at least a portion of the first expandable balloon.

In an alternative embodiment, the elongate body includes a second lumen extending from a proximal end of the elongate body to a plurality of surfaces that define openings through the elongate body adjacent the proximal end of the first expandable balloon. The plurality of struts can be coupled to a retracting wire in the second lumen through the plurality of surfaces that define the openings. The retracting wire can then be moved to pull the plurality of struts longitudinally along the elongate body so as to draw the expandable filter over and into contact with at least a portion of the first expandable balloon.

The medical catheter of the present invention can further include radial support arms coupled to first portion and the second portion of the expandable filter that can help in providing a predetermined shape to the expandable filter. In addition, the medical catheter can also include a vascular stent positioned over at least a portion of the first expandable balloon and/or positioned over at least a portion of the filter assembly and the first expandable balloon.

In an additional embodiment, the medical catheter can further include a second expandable balloon coupled to the elongate body that can be spaced apart from the first expandable balloon. The first lumen of the elongate body of the medical catheter also further includes a second outlet port in the elongate body, where the second outlet portion is in fluid communication with the second expandable balloon.

The medical device system of the present invention can include the medical catheter described herein in addition to an inflation device that includes a fluid output port to couple to the inlet port of the first lumen. The inflation device further includes a fluid pressure generator coupled to the fluid output port to deliver pressurized fluid through the fluid output port to the first expandable balloon.

The medical device and medical device system of the present invention can also be used in a method for use in surgery comprising one or more features described herein. The method can include, but is not limited to, introducing the medical device catheter into a vas, where the medical device catheter is as described herein, and inflating the expandable balloon to expand the filter assembly. The filter assembly can be expanded with the inflating of the expandable balloon to form a channel between the filter assembly and the expandable balloon through which the fluid (e.g., blood) moves. The filter assembly can then be used to filter fluid within the vas to capture particles from the fluid in the filter assembly, where the vas can include a blood vessel. When used in a blood vessel, particles in the blood moving through the vessel and into the channel can be captured with the filter assembly. In addition to inflating the filter assembly, inflating the expandable balloon can dilate a lumen of the blood vessel.

In one embodiment, inflating the expandable balloon to expand the filter assembly includes extending a portion of the expandable filter beyond the distal end of the expandable balloon. In addition, the method of using the medical device and medical device system in surgery can include deploying a stent when inflating the expandable balloon, and capturing particles with the expanded filter assembly. One or more drugs may also be released from the filter assembly into the vas when using the medical device and medical device system of the present invention.

Once the use of the filter assembly is complete, the expandable filter can then be drawn over and into contact with at least a portion of the first expandable balloon. The medical device catheter, including the captured particles (e.g., embolic material) captured during the procedure, can then be withdrawn from the vas after completion of the procedure.

The present invention also includes a method of making a medical device catheter, that includes providing an elongate body comprising at least a first lumen extending between an inlet port and an outlet port in the elongate body; coupling a first expandable balloon that includes a proximal end and a distal end to the elongate body, where the proximal end and the distal end are coupled to the elongate body, and where the outlet port is positioned between the proximal end and the distal end so as to be in fluid communication with the first expandable balloon. A filter assembly can then be provided to the medical device catheter, where the filter assembly can include an expandable filter and a plurality of struts, where the expandable filter includes a first portion coupled to a portion of the medical device catheter and a second portion coupled to the plurality of struts, where the struts tether the second portion of the expandable filter to the elongate body adjacent the proximal end of the first expandable balloon. Alternatively, the filter assembly can include an expandable filter, wherein the expandable filter comprises a first portion coupled to a portion of the medical catheter and a second portion positioned around at least a portion of the first expandable balloon to form a channel between the filter assembly and the first expandable balloon.

BRIEF DESCRIPTION OF THE DRAWINGS

FIGS. 1A-1D provide perspective views of a general embodiment of a medical device catheter in various states in a portion of a vessel according to the present invention.

FIG. 2 provides an enlarged perspective view of a general embodiment of a medical device catheter with at least a partially inflated first expandable balloon and partially deployed filter assembly according to the present invention.

DETAILED DESCRIPTION

Figure 1C:
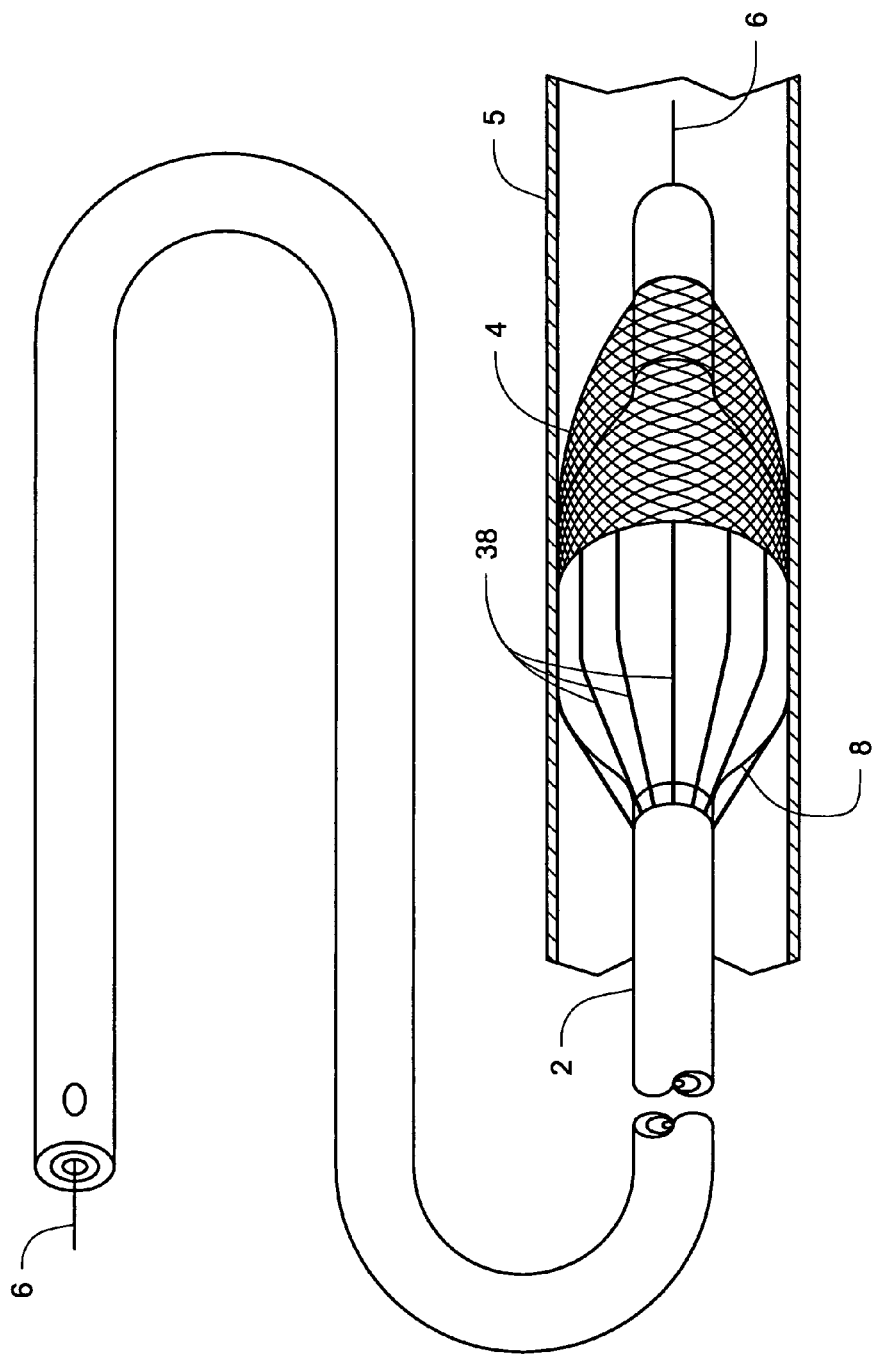

Percutaneous transluminal devices have been successfully used in treating thrombotic or atherosclerotic lesions in blood vessels. These devices include those for directional atherectomy and coronary angioplasty with or without stent deployment. In addition to being used in angioplasty, stenting, and/or atherectomy in the tubular conduits (e.g., blood vessels), percutaneous transluminal devices have also been used in treating other vascular lesions associated with, for example, carotid artery stenosis, arterial occlusive disease (especially the aorta, the iliac artery, and the femoral artery), renal artery stenosis caused by atherosclerosis or fibromuscular disease, superior vena cava syndrome, and occlusive iliac vein thrombosis resistant to thrombolysis.

One complication common to use of percutaneous transluminal devices is the dislodgment of embolic particles that occur during the treatment of the lesion in the blood vessel. This dislodgement of embolic particles has the potential of occluding downstream vessels leading to ischemic (e.g., stroke) or infarct event occurring in the organ having the occluded vessel(s). These embolic particles include calcium, intimal debris, atheromatous plaque, and/or thrombi.

The present invention provides a medical catheter, including a medical system, and method of using the medical catheter for filtering and capturing particles in fluids, including embolic particles in blood. FIGS. 1A-1D show a general embodiment of a medical device catheter in a portion of a vessel according to the present invention. The invention generally includes a balloon angioplasty catheter 2 having a filter assembly 4 attached thereto. A guidewire 6 can be used to position balloon angioplasty catheter 2 at a location within a vessel 5 (e.g., blood vessel of the vasculature) of a patient. Balloon angioplasty catheter 2 includes an expandable balloon 8 that can be used to open filter assembly 4 from an undeployed state into a deployed state at least partially downstream of expandable balloon 8, a guidewire 6 and struts 38.

FIG. 1A shows the balloon angioplasty catheter 2 and the filter assembly 4 in a pre-deployed state positioned in vessel 5 by guidewire 6. In this state, the expandable balloon 8 and the filter assembly 4 have a low cross-sectional profile relative the other portions of the balloon angioplasty catheter 2. To accomplish this, the filter assembly 4 can be packaged over the expandable balloon 8, in its deflated state, as will be discussed more fully herein.

FIG. 1B shows the expandable balloon 8 in a partially inflated state, where the inflating expandable balloon 8 begins to open the filter assembly 4.

FIG. 1C shows the expandable balloon 8 in its fully inflated state, where the filter assembly 4 becomes deployed within the vessel of the patient to essentially occupy the cross-sectional area of the vessel 5. In addition, the filter assembly 4 can be positioned relative expandable balloon 8 so as to allow embolic particles to be captured in filter assembly 4.

FIG. 1D shows the expandable balloon 8 in a partially deflated state following inflation, where the filter assembly 4 remains deployed within the vessel of the patient to essentially occupy the cross-sectional area of the vessel 5. The filter assembly 4 is shown in a position relative to expandable balloon 8 where it can capture embolic particles that are released from vessel 5 following deflation of expandable balloon 8. Once the need for the balloon angioplasty catheter 2 is complete, the filter assembly 4 can be retracted (i.e., lowered) over the deflated expandable balloon 8 to trap and contain any embolic particles captured by the filter assembly 4. The balloon angioplasty catheter 2, along with any captured embolic particles, can then be removed from the vessel 5 of the patient. These aspects of the present invention will now be more fully discussed herein.

Figure 3:
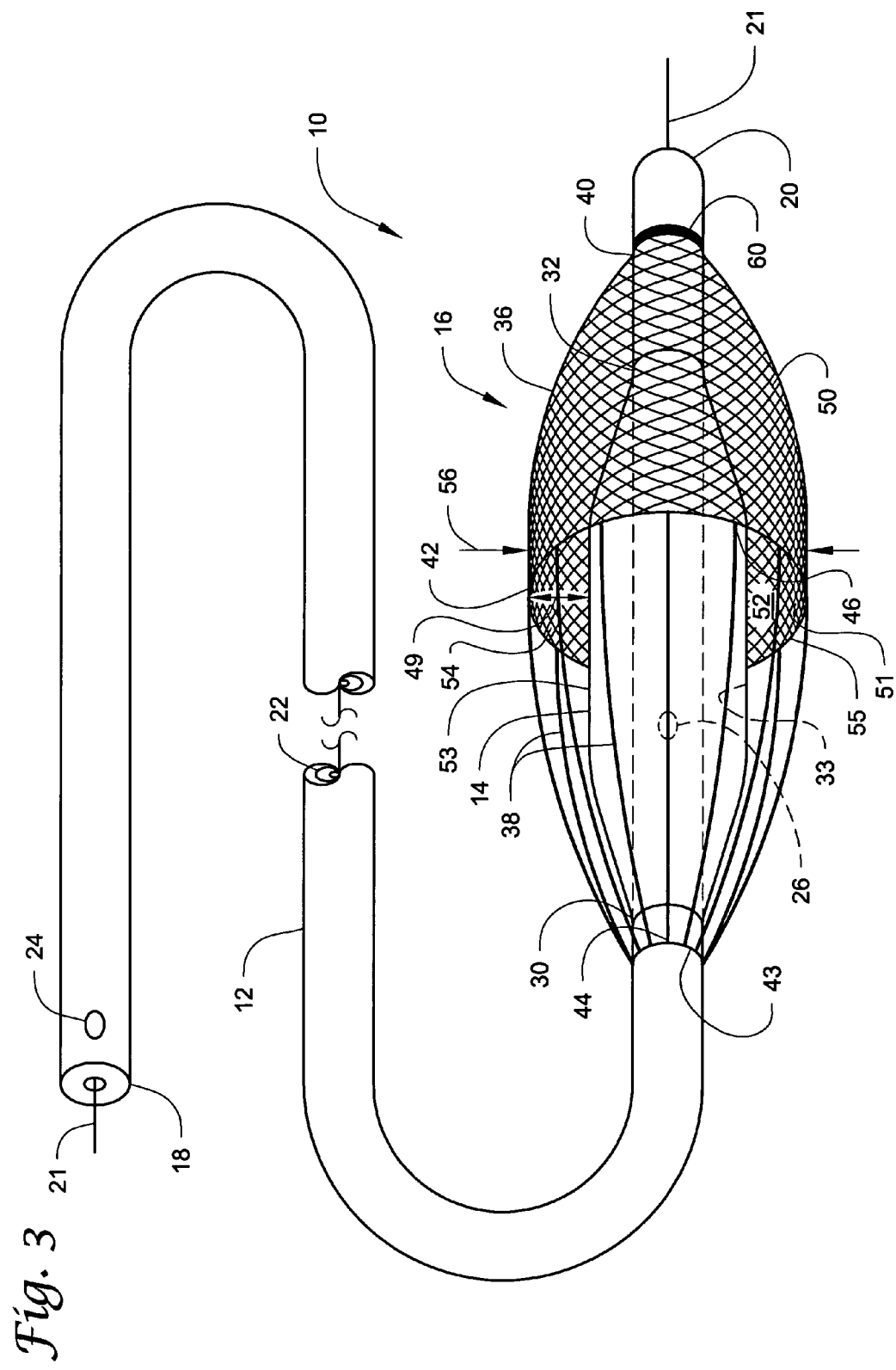
FIG. 3 provides an enlarged perspective view of a general embodiment of a medical device catheter with at least partially deflated first expandable balloon and a deployed filter assembly according to the present invention.

FIGS. 2 and 3 show additional embodiments of the medical catheter according to the present invention. FIGS. 2 and 3 provide a medical catheter 10 having an elongate body 12, a first expandable balloon 14, and a filter assembly 16. Elongate body 12 includes a proximal end 18 and a distal end 20, with first expandable balloon 14 and filter assembly 16 positioned there-between. FIG. 2 provides a general example where first expandable balloon 14 is in an inflated configuration and FIG.

3 provides a general example where filter assembly 16 has been deployed by first expandable balloon 14, now in a deflated condition.

As shown in FIGS. 2 and 3, filter assembly 16 is generally positioned over at least a portion of elongate body 12 and first expandable balloon 14. In addition, filter assembly 16 is also typically positioned proximal to distal end 20 of elongate body 12.

In one embodiment, elongate body 12 of medical catheter 10 is constructed of a medical grade polymer and/or co-polymer. Medical grade polymers and/or co-polymers for elongate body 12 can include, but are not limited to, medical grade silicone, medical grade high density silicone, polyethylene, and nylon.

Elongate body 12 can have a length between proximal end 18 and distal end 20 sufficient to allow medical catheter 10 to be positioned in any number of locations within a body of a patient. For example, elongate body 12 can have a length that is in a range of 10 cm to 200 cm. In addition, elongate body 12 includes a diameter in a range of 0.7 mm (2 French) to 4.1 mm (12 French). Elongate body 12 can also include one or more lumens that extend from proximal end 18 of elongate body 12 to one or more locations along elongate body 12, including distal end 20 of elongate body 12. The one or more lumens can be arranged concentric manner and/or an eccentric manner within elongate body 12. The one or more lumens can be used in transporting liquid (e.g., sterile saline solution) for inflating and deflating one or more expandable balloons located on elongate body, transporting cables and/or wires for manipulating structures attached to elongate body (e.g., filter assembly as will be described herein), and for allowing elongate body 12 to travel over a guidewire 21.

First expandable balloon 14 has a proximal end 30 and a distal end 32 coupled to elongate body 12. In one example, the ends of first expandable balloon 14 can be coupled to elongate body 12 through the use of an adhesive. Alternatively, the ends of first expandable balloon 14 can be coupled to elongate body 12 through the use of sonic welding techniques. Elongate body 12 further includes at least a first lumen 22 extending between an inlet port 24 and an outlet port 26. In one embodiment, inlet port 24 can be positioned at, or adjacent, proximal end 18 of elongate body 12. Inlet port 24 is in fluid tight communication with first lumen 22, and allows for fluid to pass through first lumen 22 to outlet port 26. In one example, outlet port 26 can be positioned between proximal end 30 and distal end 32 of balloon 14. This allows for fluid to pass into and out of interior portion 33 of first expandable balloon 14 through outlet port 26 to inflate and deflate first expandable balloon 14. Other configurations for placing ports 24 and 26 on elongate body 12 are also possible.

First expandable balloon 14 can be constructed of any number of polymeric materials that have been treated in any number of ways (e.g., treatments to alter and/or add compounds to the surface of balloon 14). In addition, first expandable balloon 14 can also have any number of predetermined shapes, lengths and/or diameters as are known. The selection of material, treatment, shape, length and diameter for first expandable balloon 14 will typically be guided by the patient's particular medical situation.

Examples of materials, treatments, shapes, lengths and diameters for first expandable balloon 14 include, but are not limited to, for the materials: polyethylene, polyurethane, polyethylene terephthalate (PET); for the treatments (including surface treatments) hydrophillic coatings, hydrophobic coatings, pharmaceutical coatings; for the lengths 2 mm or greater, 100 mm or less, or ranges there between; for the diameter 0.25 mm or greater, 50 mm or less, or ranges there between.

FIGS. 2 and 3 also show an embodiment of filter assembly 16 that includes an expandable filter 36 and a plurality of struts 38. Expandable filter 36 includes a first portion 40 coupled to elongate body 12 and a second portion 42 coupled to plurality of struts 38. Each of plurality of struts 38 includes a first end 44 and a second end 46. In one embodiment, first end 44 of struts 38 can be coupled to elongate body 12 at a connection region 43 on elongate body 12. As used herein, connection region 43 includes structures in at least a portion of the medical catheter 10 at which the struts 38 are coupled either directly and/or indirectly to the elongate body 12 and where force can be imparted through to move the struts 38 to retract expandable filter 36 from its deployed configuration. In addition, second end 46 of struts 38 can be coupled to second portion 42 of expandable filter 36. In one embodiment, struts 38 tether second portion 42 of expandable filter 36 to elongate body 12 adjacent proximal end 30 of first expandable balloon 14 at connection region 43.

In the present example, plurality of struts 38 pass over at least a portion of first expandable balloon 14 from second portion 42 of expandable filter 36 to connection region 43. Struts 38 are unattached to first expandable balloon 14 so as to allow each of plurality of struts 38 to move freely over balloon 14 as balloon 14 inflates and deflates. In other words, struts 38 are neither coupled to, nor attached to, expandable balloon 14. As such, struts 38 are free to move relative to expandable balloon 14.

Struts 38 of the present invention are constructed of any number of materials and have any number of structural configurations. For example, plurality of struts 38 can be constructed of a material and have a structural configuration that is different from the material and structural configuration of expandable filter 36. So for example, struts 38 could be cables and/or wires constructed of a polymer, a co-polymer and/or a metal. Examples of polymer and/or co-polymers include, but are not limited to, medical grade polymers and/or co-polymers such as polyurethane, polyethylene, nylon, and polyethylene terephthalate (PET).

In an alternative embodiment, struts 38 could be formed from a medical grade metal or metal alloy. Examples of such medical grade metal and metal alloys include, but are not limited to, stainless steel (e.g., examples of medical grade stainless steel such as stainless steel 316), nitinol, and/or noble metals (e.g., gold or platinum).

In addition, struts 38 are also sufficiently flexible so as not to interfere with the inflation and deflation of first inflatable balloon 14. Also, struts 38 have sufficient tensile strength so as to allow expandable filter 36 to be securely tethered to elongate body 12 when expandable filter 36 has been deployed, and to allow the expandable filter to be contracted by a pulling force imparted to struts 38 through connection region 43, as described herein. To that end, struts 38 can have a cross-sectional profile, such as a diameter, having a dimension sufficient to provide struts 38 with the desired amount of both flexibility and tensile strength. For example, struts 38 can have a diameter of 0.254 mm or greater, 2.032 mm or less, or in a range of 0.254 mm to 2.032 mm. The length of struts 38 will be dependent upon both the configuration of filter assembly 16 and possibly on the length of elongate body 12. As will be appreciated, the type of material, structural configuration and the dimension of the cross-sectional profile of struts 38 will contribute to the flexibility and tensile strength of struts 38.

In an alternative embodiment, struts 38 of the present invention are constructed from the same material used to form expandable filter 36. In this embodiment, second portion 42 of expandable filter 36 and second end 46 of struts 38 are both formed of the same material and can have essentially the same structural configuration. For example, the material of expandable filter 36 can be contiguously integrated into and form struts 38. Alternatively, struts 38 can be formed of expandable filter 36 material that has been structurally modified. For example, expandable filter 36 material can be twisted into a cable like structure so as to form struts 38. Other structural modifications are also possible.

Expandable filter 36 includes a flexible network 50 having suitable physical characteristics for use with the present invention. For example, flexible network 50 can have mesh openings formed from a woven or a knit material. Alternatively, flexible network 50 can have mesh openings formed from predetermined perforations, or cuts, made in sheets of material having suitable physical characteristics for use with the present invention. Suitable materials for use in flexible network 50 include, but are not limited to, metal, metal alloys, polyesters, polyurethanes, polypropylene and polyethylene terephthalate. Other metal and polymer materials are also possible.

These materials can be in the form of strands of the material that are woven or knit into flexible network 50. Alternatively, these materials can be in a sheet form that are cut or perforated to form the openings of flexible network 50. For example, flexible network 50 can be formed from a sheet of material that is laser cut to form the mesh openings. Other meshes known in the art, which have the desired physical characteristics, are also suitable. There can be a variety of mesh surface areas for expandable filter 36 and mesh opening sizes for flexible network 50. For example, the mesh surface area for expandable filter 36 can include mesh areas in a range of 0.01 $cm^2$ or greater, 200 $cm^2$ or less, or ranges of these values, such as a range of 0.01 $cm^2$ to 200 $cm^2$.

The size of the mesh openings for flexible network 50 can also have a variety of size and shapes. For example, the size of the mesh opening can have a range of can include mesh areas in a range of 25 $\mu m^2$ to 150 $\mu m^2$, where mesh openings in a range of 75 $\mu m^2$ to 100 $\mu m^2$ are preferred values. In one example, the mesh opening is selected so as not to greatly impede the flow of blood through the flexible network 50 of the expandable filter 36. Shapes of the openings as defined by the mesh can include square, irregular, rectangular, triangular, circular, polygonal, and/or varying combinations of these shapes. Maximum dimensional values for the shapes can be 20 $\mu m$ or greater, 200 $\mu m$ or less, or in a range of 20 $\mu m$ to 200 $\mu m$. Other shapes are also possible.

The strands and/or the sheet of the material forming flexible network 50 can also have a variety of thicknesses. For example, the thickness of the material of the flexible network 50 is in a range of 10 $\mu m$ to 100 $\mu m$. In addition, the material of the flexible network 50 can have a hardness in a range of 20D to 100 D, as measured with a Durometer using the Shore D scale. Measurements of hardness were made on a Dial Durometer hardness tester, where the measurements were taken at room temperature (about 20° C.). A preferred material for flexible network 50 is a 60D-72D durometer nylon monofilament, and about 0.0005 to 0.001 diameter. Struts 38 can also be formed from the same material and, in a preferred embodiment, are about 0.004 inches in diameter.

In the deployed state, second portion 42 of expandable filter 36 is capable of expanding to an outer diameter of at least 5 cm. Alternatively, second portion 42 of expandable filter 36 is capable of expanding to an outer diameter having a value of the maximum diameter of expandable balloon 14 (i.e., the diameter at the highest pressure balloon inflation). In addition, the size of expandable filter 36 can be selected so that the perimeter of expandable filter 36 can be flush with the inner surface of the patient's vessel wall. The exact outer diameter of expandable filter 36 will be dependent upon the size of the patient being treated and/or the location of where the treatment is to take place.

Expandable filter 36 can be formed into any number of desired shapes. For example, expandable filter 36 can have a conical shape, a semi-hemispherical shape, semi-elliptical, or other shape that defines a volume through which fluids potentially having particles (e.g., blood having emboli) can flow. In addition, anticoagulants, such as heparin and heparinoids, may be applied to or integrated into the surface of expandable filter 36 to reduce the chances of blood clotting on network 50. Anticoagulants other than heparinoids also may be used. The anticoagulant may be painted or sprayed onto the network. A chemical dip comprising the anticoagulant also may be used. Other methods known in the art for applying chemicals to network 50 may be used.

The relative distance between first portion 40 of expandable filter 36 and distal end 32 of first expandable balloon 14 can also vary depending upon desired application of the present invention. For example, first portion 40 of expandable filter 36 can be separated from distal end 32 of first expandable balloon 14 by a predetermined distance. In one embodiment, the predetermined distance can have a value of 20 millimeters (mm) or less. Predetermined distances in this range allow for fluid flowing past first expandable balloon 14 and into expandable filter 36 to open and maintain the shape of deployed expandable filter 36 as will be discussed herein. In addition, the distal end 20 of elongate body 12 may need to be longer than is typical so as to allow for the relative positioning of first expandable balloon 14 and expandable filter 36.

Coupling first portion 40 of expandable filter 36 to elongate body 12 can be accomplished in any number of ways. For example, first portion 40 of expandable filter 36 can be secured to elongate body 12 through the use of an adhesive, such as epoxies, cyanoacrylate adhesives, ultra violet (UV) curing adhesives, anaerobics adhesives, hot melt adhesives, or other known medical grade adhesives.

Alternatively, first portion 40 of expandable filter 36 can be fused to elongate body 12 through the use of to sonic or thermal welding. In an additional embodiment, a band 60 can be used to secure (e.g., clamp) first portion 40 of expandable filter 36 to elongate body 12. Band 60 can be made of either a polymer, a metal or a metal alloy. Optionally, band 60 can be radiopaque to allow for its position to be detected within the patient. It is also possible to secure first portion 40 of expandable filter 36 to elongate body 12 through any combination of described, or other known techniques such as elastic or compression fit.

Expandable filter 36 is also attached to elongate body 12 at connection region 43 through the use of plurality of struts 38. As discussed herein, second end 46 of plurality of struts 38 can be coupled to second portion 42 of expandable filter 36. Coupling these components can be accomplished in any number of ways. For example, second end 46 of plurality of struts 38 can be secured directly to second portion 42 of expandable filter 36 through the use of an adhesive. Examples of suitable adhesives include, but are not limited to, epoxies, cyanoacrylate adhesives, ultra violet (UV) curing adhesives, anaerobic according to the present invention adhesives, hot melt adhesives, or other known medical grade adhesives. Alternatively, second end 46 of plurality of struts 38 can be fused to second portion 42 of expandable filter 36 through the use of to sonic or thermal welding. In addition, as discussed herein struts 38 can be formed of the same material used in expandable filter 36, where the material forming struts 38 can be the same material that forms filter 36.

In an additional embodiment, second portion 42 of expandable filter 36 positioned around first expandable balloon 14 forms a channel 49 (shown in FIG. 3, where a portion of the network 50 illustrated in FIG. 3 has been removed to better show channel 49) between filter assembly 16 and first expandable balloon 14. In the present embodiment, channel 49 can be formed between an inner surface 51 of expandable filter 36 and an outer surface 53 of first expandable balloon 14, as shown in FIG. 3.

Second portion 42 of expandable filter 36 can further include a lip 55. In one embodiment, when expandable filter 36 is deployed, lip 55 defines an opening 52 (shown in FIG. 3) of channel 49, where channel 49 includes a volume 54 (shown in FIG. 3) defined by expandable filter 36. In one embodiment, lip 55 has a predetermined shape and a predetermined size, where both the shape and the size of lip 55 depend upon the location and use of filter assembly 16. For example, predetermined shape of lip 55 includes a circular shape having a diameter 56 no larger than about a diameter 58 of first expandable balloon 14 in its inflated condition (e.g., FIG. 2). Other predetermined shapes and dimensions are also possible.

Lip 55 of expandable filter 36 can be constructed from any number of materials and have any number of structural configurations. For example, lip 55 can be constructed of a material having a different cross-sectional shape and/or dimension than either of struts 38 and/or expandable filter 36. In addition, lip 55 can be constructed not only of a material having a different cross-sectional shape and/or dimensions, but lip 55 can be constructed of a material that is either the same or different material as struts 38 and/or expandable filter 36.

In an additional embodiment, lip 55 of expandable filter 36 can be used to connect filter 36 to elongate body 12 at connection region 43. For example, second end 46 of plurality of struts 38 can be coupled to points along lip 55, where plurality of struts 38 can be coupled to lip 55 through the use of adhesives or through welding techniques (e.g., sonic or laser), as described herein.

Connection region 43 can include a variety of structures, either attached to elongate body 12 or integrated directly into elongate body 12, that couple first end 44 of struts 38 to elongate body 12. In addition, connection region 43 can also include structures that allow for struts 38 to be used to retract expandable filter 36 from its deployed configuration.

Figure 4:
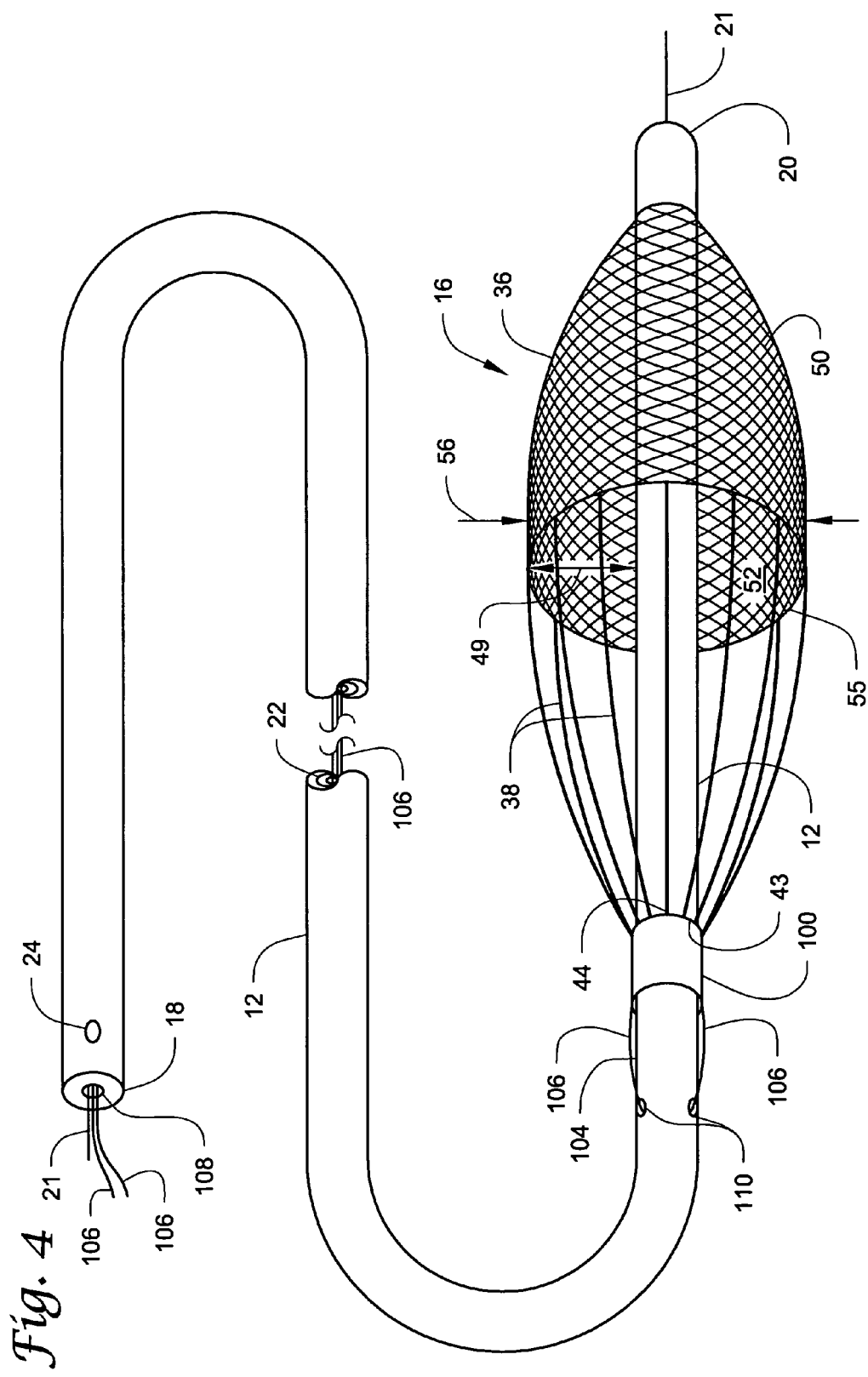
FIG. 4 provides a perspective view of a general embodiment of a medical device catheter that includes a collar in the connection region and a deployed filter assembly according to the present invention.

FIG. 4 depicts an embodiment of the filter assembly 16 (see FIG. 2) that includes a collar 100 mounted over an exterior surface 104 of elongate body 12. First end 44 of struts 38 can be coupled to collar 100 through the use of adhesives or through welding techniques (e.g., sonic or laser), as described herein.

In the present example, collar 100 can slide over exterior surface 104 of elongate body 12. In one embodiment, collar 100 can be slid along elongate body 12 in the direction of proximal end 18 of body 12 to allow struts 38 to pull on expandable filter 36 so filter 36 can be retracted. As used herein, "retracting" expandable filter 36 includes reducing diameter 56 of opening 52 of filter 36 relative to filter 36 diameter 56 when fully deployed in the patient.

Collar 100 can have a length of 0.5 µm or greater, 200 cm or less, or in a range of 0.5 µm to 200 cm. Collar 100 can be slid over exterior surface 104 of elongate body 12 through the use of wires 106. In one example, wires 106 travel in lumen 108 from proximal end 18 to outlet openings 110 through the elongate body 12. Wires 106 can then be slid through lumen 108 to change the position of expandable filter 36. For example, wires 106 can be used to retract expandable filter 36 as defined herein.

Wires 106 can be constructed of one or more of the polymer, co-polymers and/or metal materials recited herein. Collar 100 can have a tubular construction of polyurethane, nitinol, polyesters, silicones, or fabric of polymer and/or metal construction. In addition, lumen 108 can also be used with guidewire 21.

Figure 5:
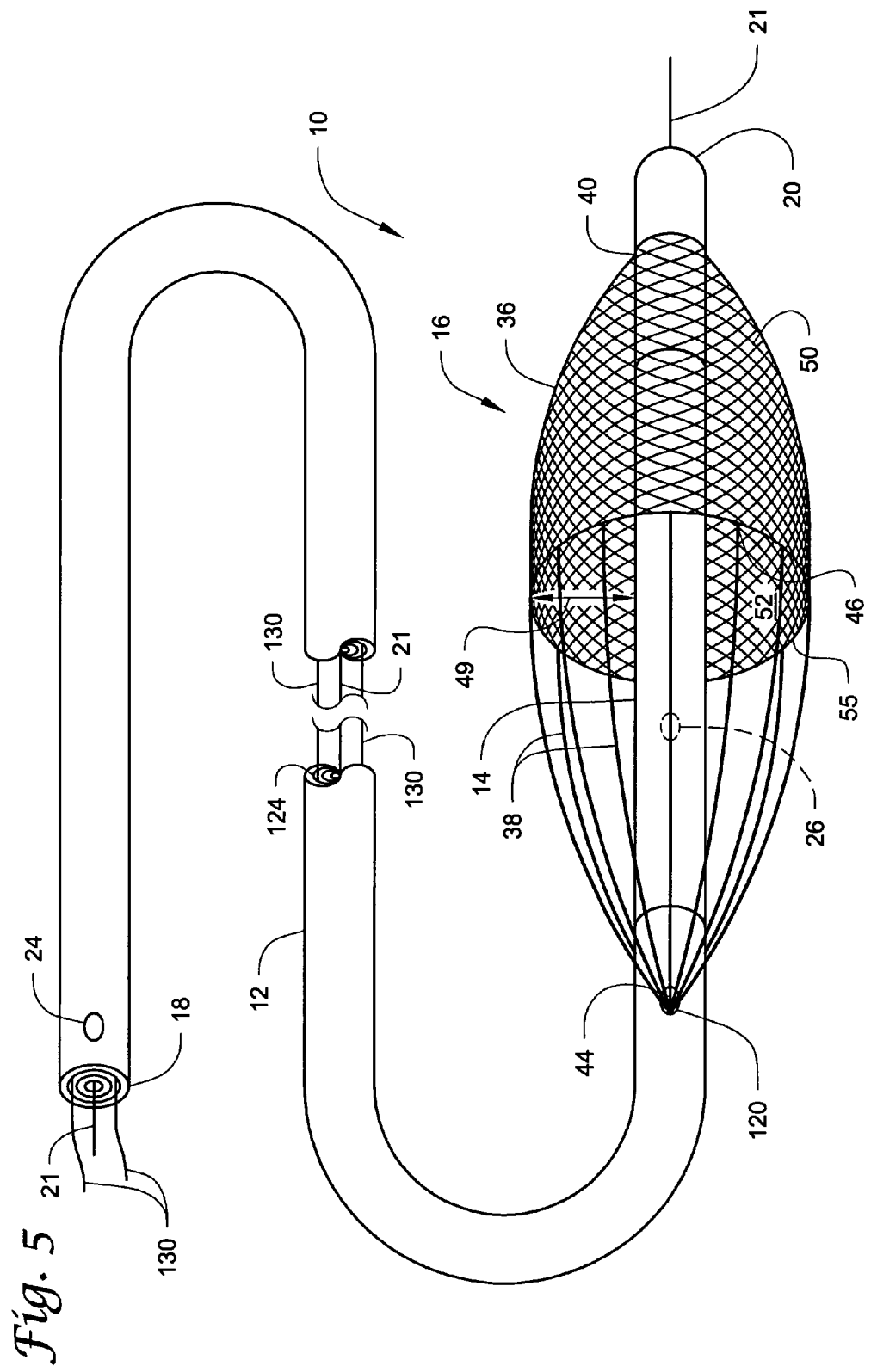
FIG. 5 provides a perspective view of an additional embodiment of filter assembly in which one or more surfaces of elongate body define openings into at least one lumen of the elongate body according to the present invention.

FIG. 5 depicts an additional embodiment of filter assembly 16 in which one or more surfaces of elongate body 12 define openings 120 through body 12 into at least one lumen 124. As shown in FIG. 5, struts 38 travel through openings 120 in elongate body 12 to position first end 44 of struts 38 in lumen 124.

In one example, first end 44 of struts 38 positioned in lumen 124 can be coupled to a retracting line 130 that extends beyond proximal end 18 of body 12. Retracting line 130 can be used to pull on struts 38 to retract expandable filter 36. In an alternative embodiment, two or more of first end 44 of struts 38 are wound together so that retracting line 130 takes the form of a cable. Alternatively, retracting line 130 is a wire to which first end 44 of struts 38 can be coupled through the use of adhesives or through welding techniques (e.g., sonic or laser), as described herein. Regardless of its structure, retracting line 130 has a diameter that is sufficiently smaller than the diameter of lumen 124 so as to allow retracting line 130 to move within lumen 124.

In addition, retracting line 130 has a sufficiently high tensile strength to prevent line 130 from breaking and/or stretching as line 130 is pulled to retract expandable filter 36. Examples of suitable materials for retracting line 130 include, but are not limited to, the polymer, co-polymers, metal and/or metal alloys described herein.

Figure 6:
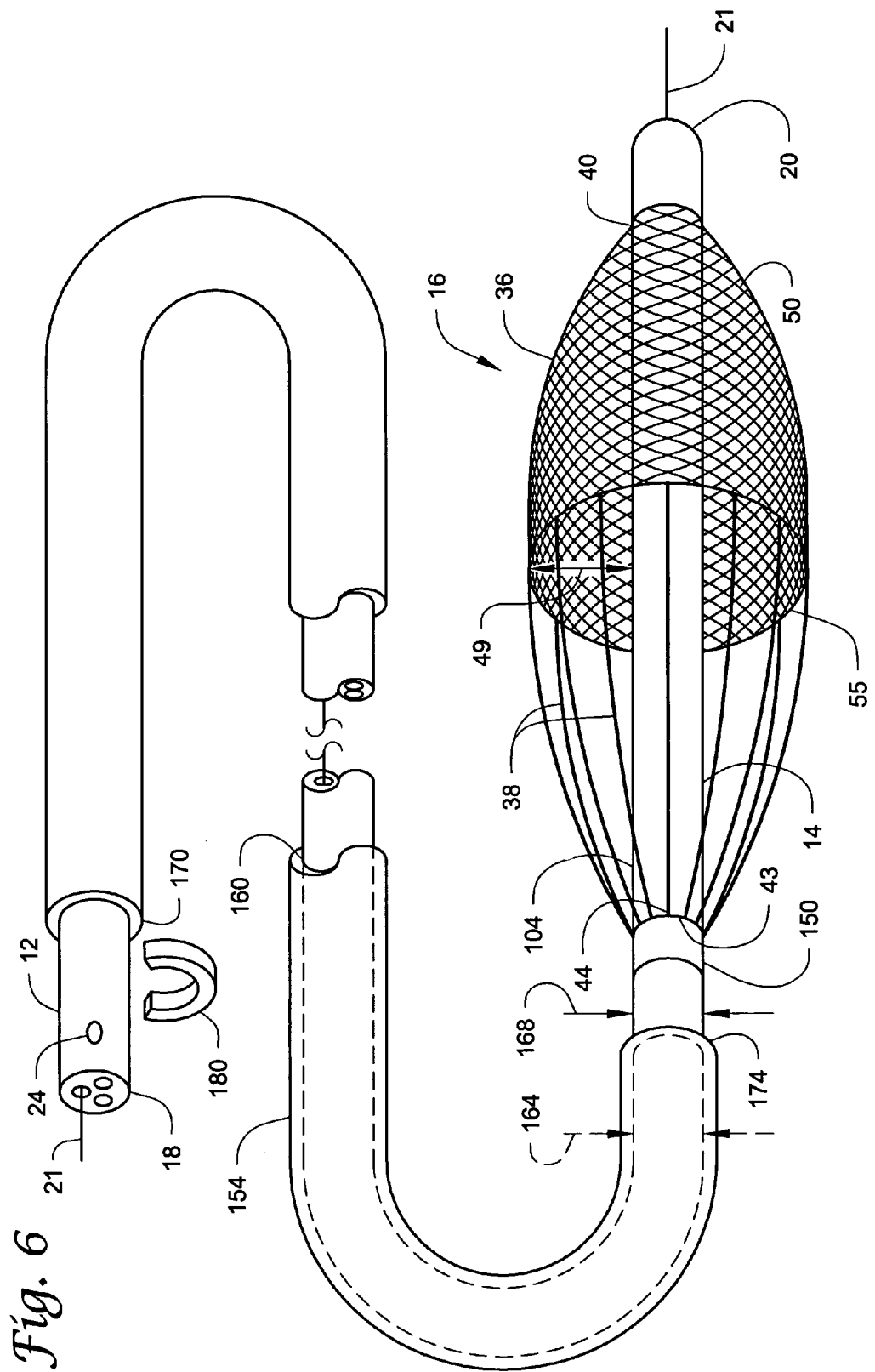
FIG. 6 provides a perspective view of an additional embodiment of the connection region according to the present invention.

FIG. 6 shows another example of connection region 43 according to the present invention. The connection region 43 in FIG. 6 includes first end 44 of struts 38 coupled to elongate body 12. For example, first end 44 of struts 38 can be coupled to elongate body 12 as described herein. Alternatively, first end 44 of struts 38 can be fused to elongate body 12 through the use of to sonic or thermal welding. In an additional embodiment, a band 150 can be used to secure (e.g., clamp) first end 44 of struts 38 to elongate body 12. In one embodiment, band 150 can be made of either a polymer and/or a metal, where band 150 is radiopaque to allow for its position to be detected when positioned within the patient. It is also possible to secure first end 44 of struts 38 to elongate body 12 through any combination of described, or other known techniques.

The embodiment shown in FIG. 6 also includes a catheter 154. Catheter 154 includes a lumen 160 having an inner diameter 164 that is greater than outer diameter 168 of elongate body 12. In one embodiment, catheter 154 can be completely positioned over elongate body 12 (i.e., elongate body 12 is positioned in lumen 160 of catheter 154). As shown in FIG. 6, a proximal end 170 of catheter 154 is positioned at or positioned distally from proximal end 18 of elongate body 12 when a distal end 174 of catheter 154 is proximal connection region 43.

In one embodiment, catheter 154 can be moved over elongate body 12 from force applied at proximal end 170 of catheter 154 until lumen 160 of catheter 154 contacts struts 38 in connection region 43. As catheter 154 continues to be advanced towards distal end 20 of body 12, struts 38 are drawn between exterior surface 104 of elongate body 12 and the inner surface of lumen 160. As this happens, expandable filter 36 retracts. Once retracted, a locking collar 180 can be used with either elongate body 12 or catheter 154 to prevent the relative movement of elongate body 12 and catheter 154. The use of locking collar 180, however, is not necessary.

Figure 7:
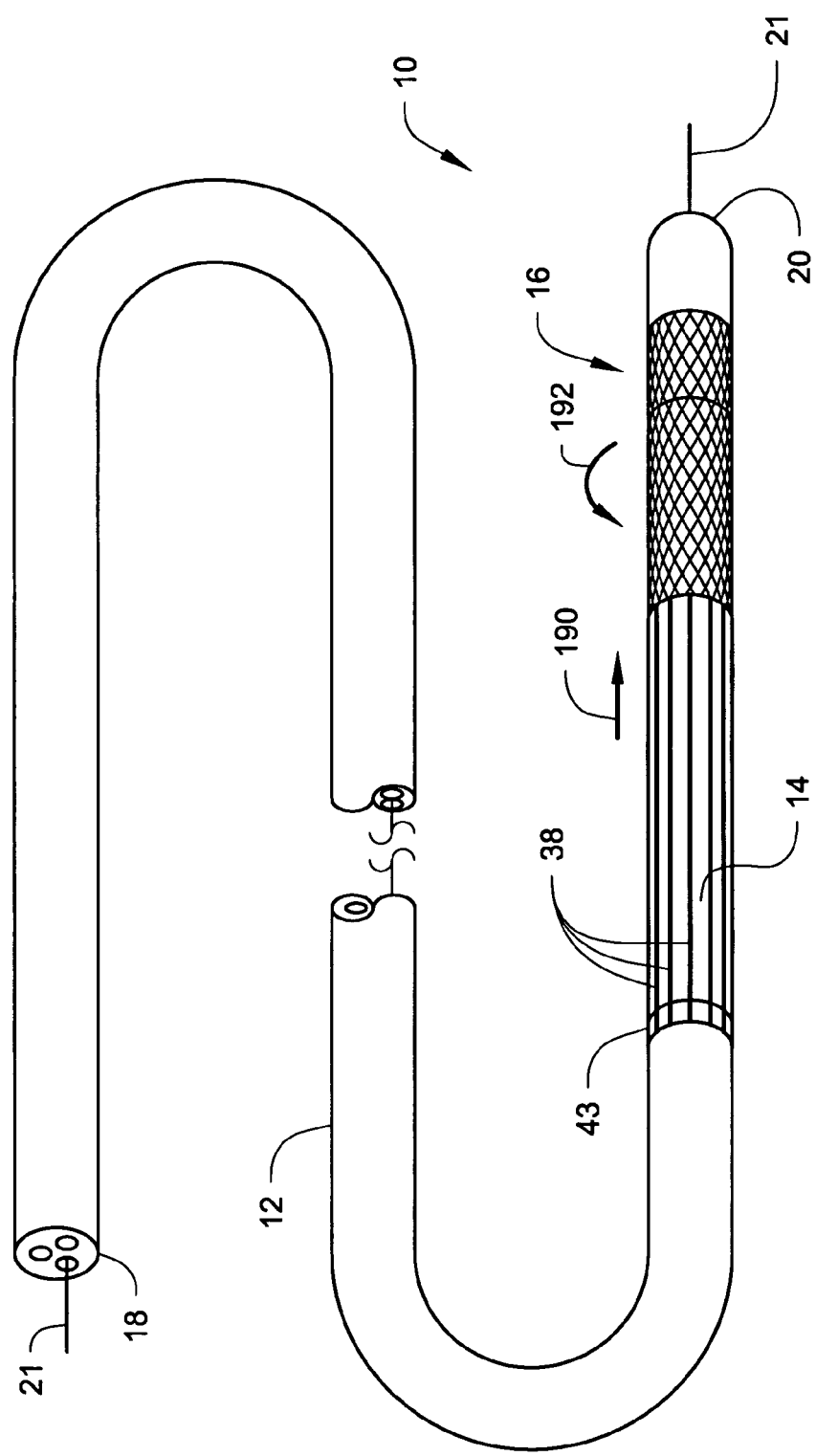
FIG. 7 provides a perspective view of an embodiment of medical catheter according to the present invention where the both filter assembly and first expandable balloon are in there undeployed state.

FIG. 7 shows an embodiment of medical catheter 10 according to the present invention where the both filter assembly 16 and first expandable balloon 14 are in their undeployed state. In this condition, both first expandable balloon 14 and filter assembly 16 are configured so as to have as low a profile as possible relative to elongate body 12. In one example, both first expandable balloon 14 and filter assembly 16 are folded along longitudinal axis 190 of elongate body 12 and then wrapped 192 around elongate body 12 perpendicular to longitudinal axis 190 of elongate body 12. Other configurations for packaging first expandable balloon 14 and filter assembly 16 on elongate body 12 are also possible.

Figure 8:
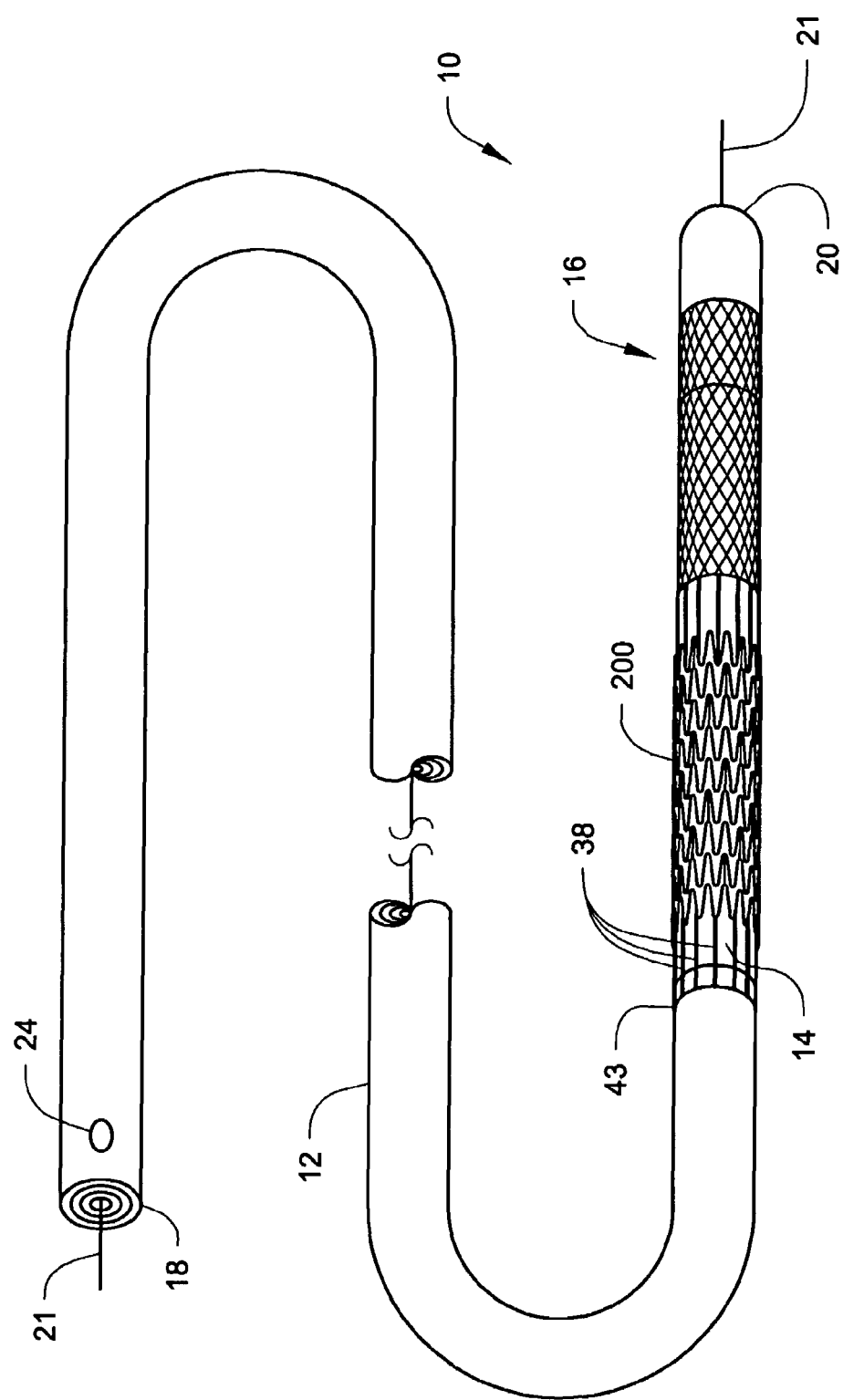
FIG. 8 provides a perspective view of an additional embodiment of medical catheter according to the present invention where there is a stent positioned over at least a portion of catheter.

FIG. 8 shows an additional embodiment of medical catheter 10 according to the present invention where in addition to both filter assembly 16 and first expandable balloon 14 being in their undeployed state, there is also included a stent 200 positioned over at least a portion of catheter 10. In one embodiment, stent 200 can be a vascular stent for opening and supporting a portion of a blood vessel. In one embodiment, stent 200 can be crimped over both first expandable balloon 14 and at least a portion of struts 38 to secure stent 200 to elongate body 12. Stent 200 can then be deployed, along with filter assembly 16 as first expandable balloon 14 is inflated, as described herein.

Figure 9:
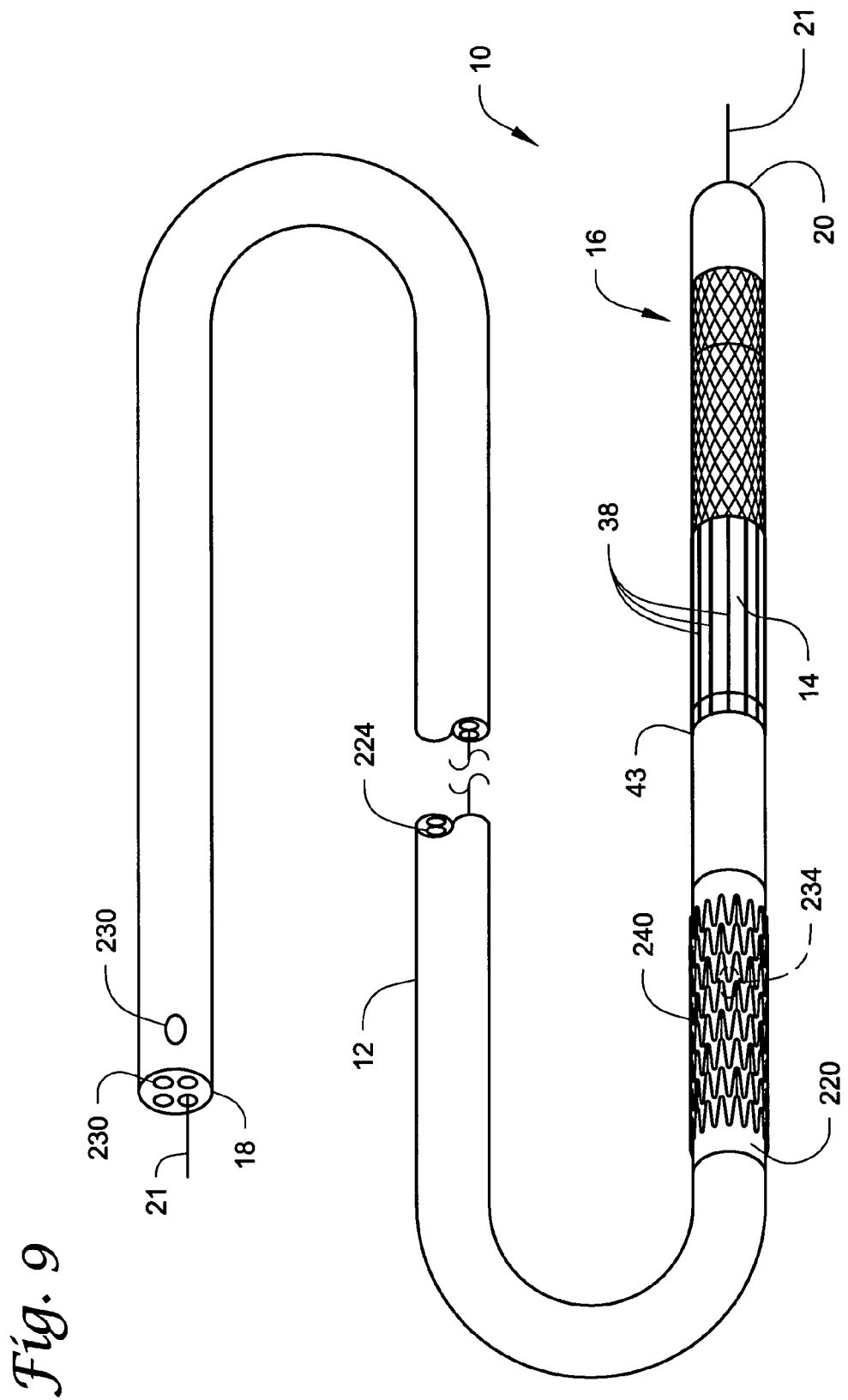
FIG. 9 provides a perspective view of an additional embodiment of medical catheter according to the present invention that includes a second expandable balloon.

FIG. 9 shows an additional embodiment of medical catheter 10 according to the present invention. Once again, both filter assembly 16 and first expandable balloon 14 are shown in their undeployed state. In addition, medical catheter 10 shown in FIG. 9 further includes a second expandable balloon 220. Second expandable balloon 220 can be coupled to elongate body 12 in a similar manner as first expandable balloon 14. In addition, second expandable balloon 220 can include the same features and configurations as those described herein for first expandable balloon 14.

In addition, elongate body 12 can further include a second lumen 224 extending between a second inlet port 230 and a second outlet port 234 in elongate body 12. In one embodiment, second inlet port 230 can be positioned at, or adjacent, proximal end 18 of elongate body 12. Second inlet port 230 can be in fluid tight communication with second lumen 224 to allow for fluid to pass through second lumen 224 to second outlet port 234. In one example, second outlet port 234 can be positioned between the proximal end and the distal end of second balloon 220 to allow for fluid to pass into and out of the interior portion of second expandable balloon 220 to inflate and deflate second expandable balloon 220. Other configurations for placing ports 230 and 234 on elongate body 12 are also possible.

Catheter 10 in FIG. 9 also includes a stent 240 positioned on medical catheter 10. In one embodiment, stent 240 can be a vascular stent for opening and supporting a portion of a blood vessel. In one embodiment, stent 240 can be crimped over second expandable balloon 220 to secure stent 240 to elongate body 12. When deploying stent 240, first expandable balloon 14 can be inflated to deploy filter assembly 16 that is positioned distal second expandable balloon 220. Once filter assembly 16 is deployed, first expandable balloon 14 can be deflated. The deployed filter assembly 16 is then prepared to filter the fluid (e.g., blood) that moves past second expandable balloon 220. Second expandable balloon 220 can then be inflated to deploy stent 240 at a desired location. As filter assembly is located "downstream" of first and second expandable balloons 14 and 220 and stent 240, expandable filter 16 is capable of filtering the fluid (i.e., blood) for any released particles.

Figure 10:
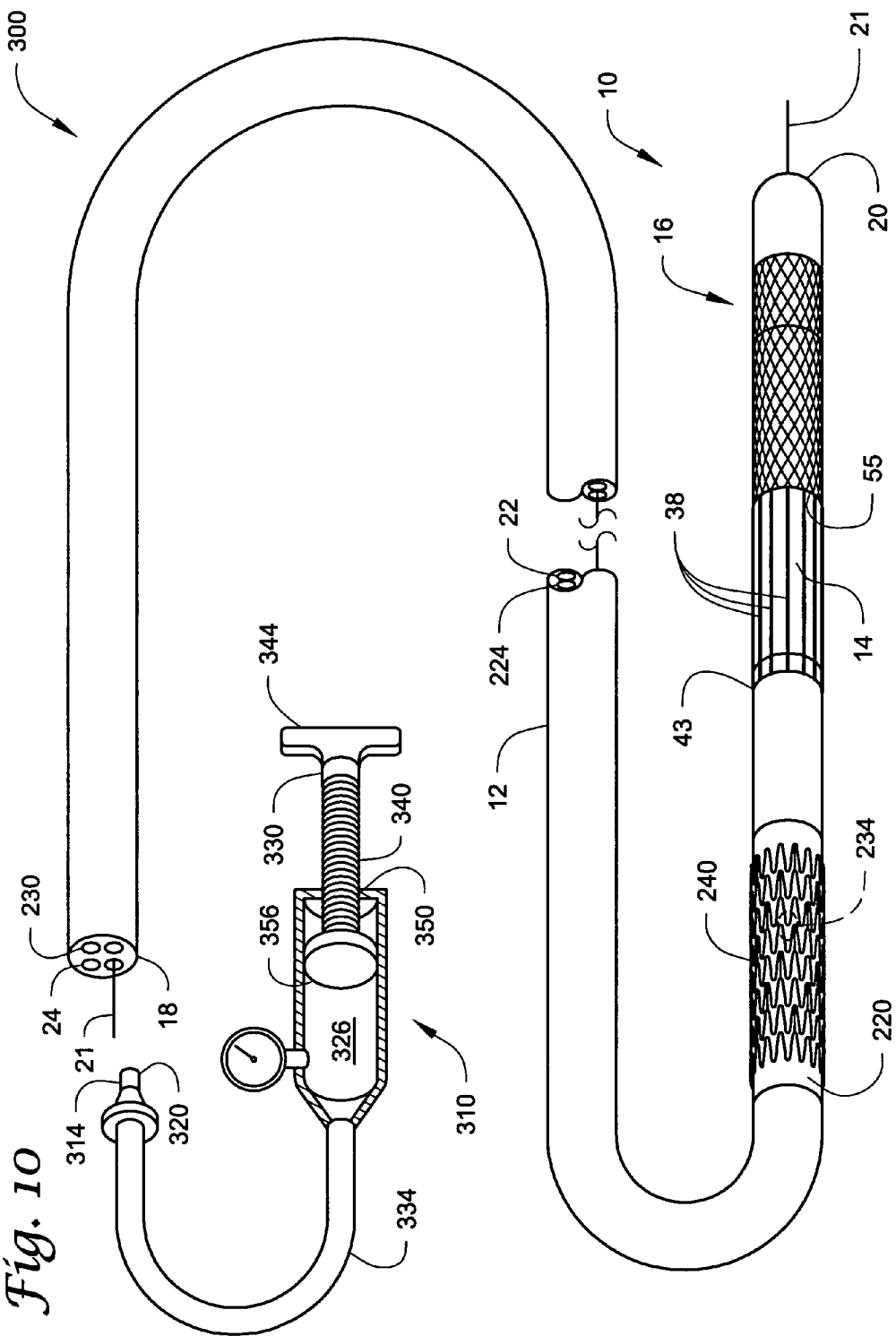
FIG. 10 provides a perspective view of a medical device system 300 according to the present invention that includes a medical catheter and an inflation device according to the present invention.

FIG. 10 shows an additional embodiment of a medical device system 300 according to the present invention. Medical device system 300 includes medical catheter 10 according to the present invention where first lumen 22 of elongate body 12 further includes second outlet port 234 in elongate body 12. Medical catheter 10 in FIG. 10 shows both first expandable balloon 14 and second expandable balloon 220 coupled to elongate body 12, where first and second expandable balloons, 14 and 220, are spaced apart from each other. As with the previous example of FIG. 10, second outlet port 234 is in fluid communication with second expandable balloon 220.

Medical system 300 further includes an inflation device 310. Inflation device 310 can be used in any of the embodiments of medical catheter 10 of the present invention. Inflation device 310 includes a fluid output port 314 that can be reversibly coupled to the inlet port 24 of first lumen 22 and/or second inlet port 230 of second lumen 224, or any other lumen of medical catheter 10 that is intended to transport fluid. In one example, fluid output port 314 has a distal tip 320 that can reversibly lock in fluid tight communication to the inlet port of first lumen 22 and/or second inlet port 230 of second lumen 224 of medical catheter 10 according to the present invention.

Inflation device 310 also includes a fluid reservoir 326 to which is coupled a fluid pressure generator 330 and outlet tubing 334. In operation, fluid pressure generator 330 can be used to develop pressure in fluid reservoir 326, which causes fluid to move through outlet tubing 334 to output port 314 and into inlet port (24 and/or 230) of medical catheter 10. Fluid pressure developed with fluid pressure generator 330 can be used to deliver pressurized fluid through fluid output port 314 to either first expandable balloon 14 and/or second expandable balloon 220. In one embodiment, the pressurized fluid provides a force to inflate at least first expandable balloon 14 and filter assembly 16 of the present invention.

In one embodiment, fluid pressure generator 330 includes a threaded shaft 340 having a handle 344, where threaded shaft 340 interfaces with a corresponding set of threads, shown generally at 350, on generator 330. Threaded shaft 340 is also attached to a fluid tight plunger 356 in fluid reservoir 326, where fluid tight plunger 356 moves in fluid reservoir 326 as handle 344 is turned. Other types of inflation devices are also known that would be suitable for use with present system 300.

As discussed herein, the elements of filter assembly 16 are attached to elongate body 12 of medical catheter 10, and not to first expandable balloon 14. One reason for this configuration is to allow filter assembly 16 to be deployed through the use of first expandable balloon 14. In one example, first expandable balloon 14 pushes filter assembly 16 open as first expandable balloon 14 is inflated. In this situation, as first expandable balloon 14 begins to inflate it contacts struts 38, expandable filter 36, and, if present, lip 55. Once contact is made, the force of the inflating first expandable balloon 14 unwraps filter assembly 16, where struts 38 and expandable filter 36 slide along at least a portion of the exterior surface of inflating first expandable balloon 14. So, the force of the inflating first expandable balloon 14 is used to deploy filter assembly 16. It is also possible to use a medical grade lubricant between first expandable balloon 14 and at least a portion of filter assembly 16 to aid in deploying filter assembly 16. The use of the medical grade lubricant, however, is not necessary.

In addition to first expandable balloon 14, filter assembly 16 is also partially deployed by the fluids flowing over first expandable balloon 14 towards filter assembly 16. In one embodiment, the fluid flow causes filter assembly 16 to expand to its fully deployed state. Once deployed, expandable filter 36 can be held open by fluid moving through volume 54 (shown in FIG. 3) defined by expandable filter 36. In addition, lip 55 can also assist in keeping expandable filter 36 deployed when the fluid flow slows and/or stops if first expandable balloon 14 and/or second expandable balloon 220 are inflated and/or reinflated.

Figure 11:
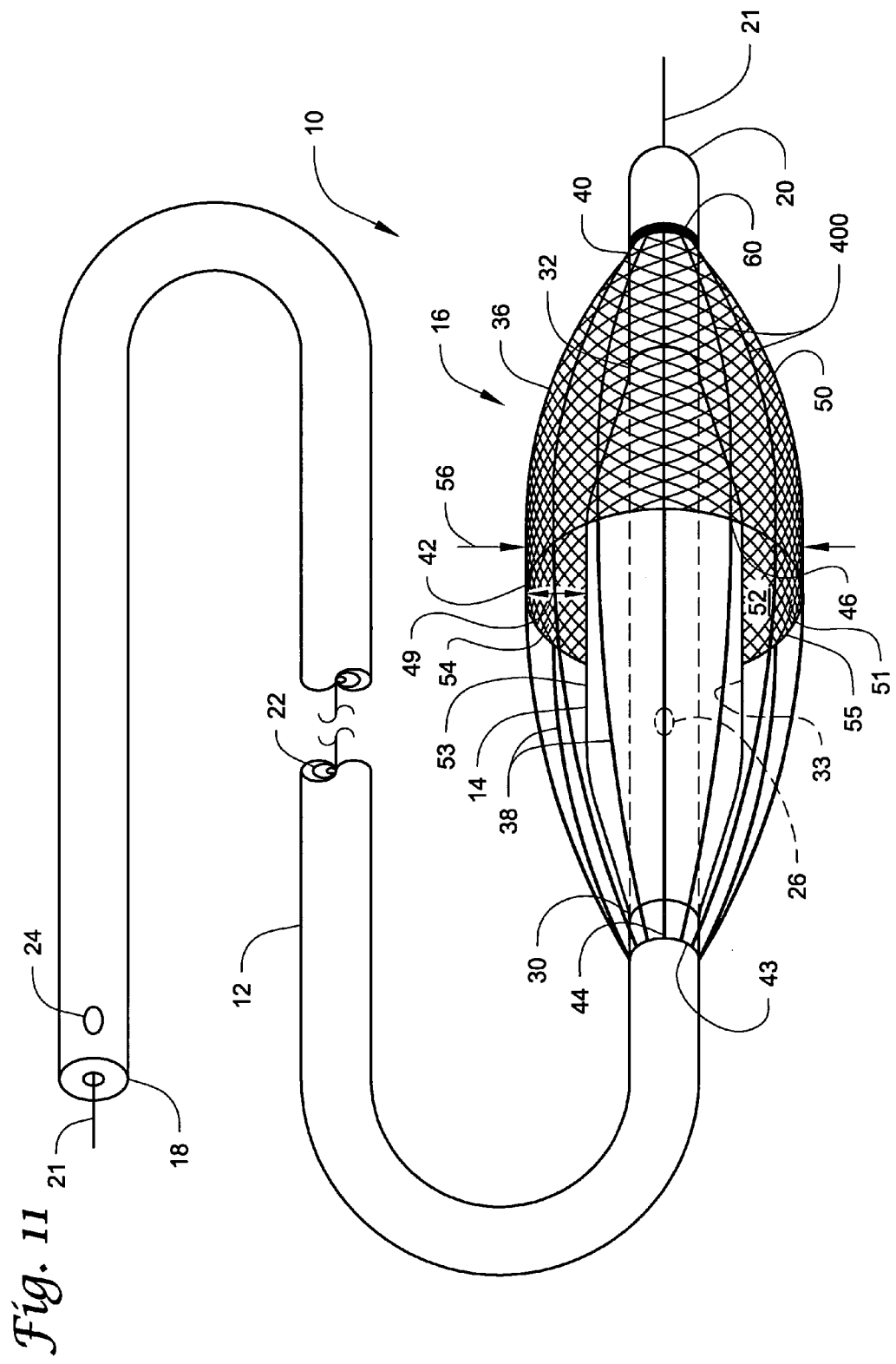
FIG. 11 provides a perspective view of a medical catheter according to the present invention where the filter assembly of the present invention further includes radial support arms.

FIG. 11 shows an additional embodiment of a medical catheter 10 according to the present invention as described herein. Medical catheter 10 shown in FIG. 11 provides an example where filter assembly 16 of the present invention further includes radial support arms 400. In one embodiment, radial support arms 400 can provide for both support and a predetermined shape to expandable filter 36. To accomplish this, radial support arms 400 are formed of a material and/or have a profile shape that allows arms 400 to have a stiffness sufficient to hold expandable filter 36 in any of the shapes described herein. In one example, the radial support arms can be formed of any number of polymeric or metal materials, including, but not limited to, urethanes, nylons, silicones, polyesters or any other polymeric or metal material described herein.

In one embodiment, radial support arms 400 can be coupled to first portion 40 and second portion 42 of expandable filter 36. Radial support arms 400 can be coupled to lip 55 when present. In addition, it is possible that the radial support arms can be coupled to the expandable filter at points between first portion 40 and second portion 42. In one embodiment, radial support arms 400 can be coupled to expandable filter 36 through the use of adhesives or through welding techniques (e.g., sonic or laser), as described herein.

Figure 12:
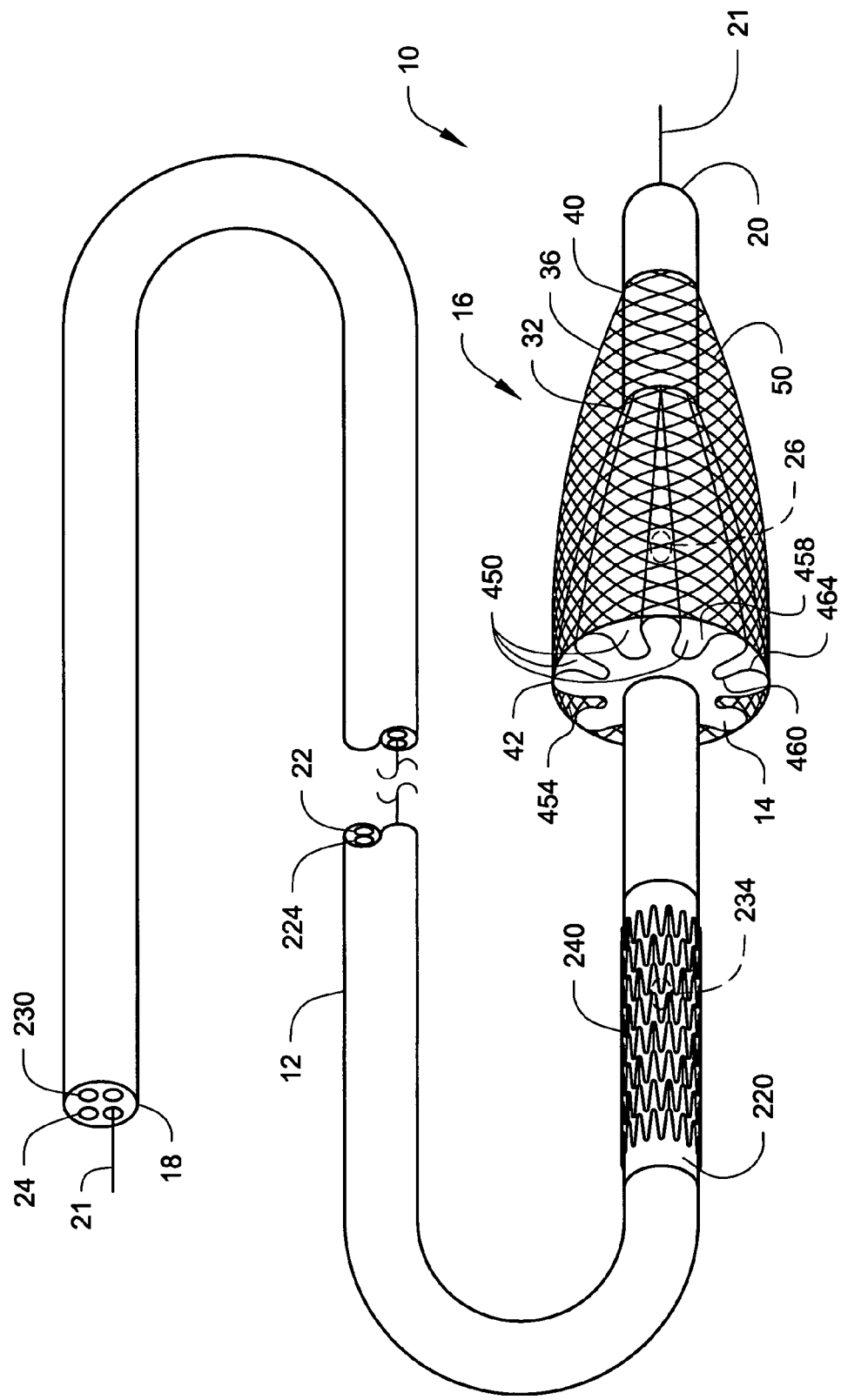
FIG. 12 provides a perspective view of a medical catheter that includes channels according to the present invention.

FIG. 12 shows an additional embodiment of medical catheter 10 according to the present invention where struts 38 are not used. As described herein, medical catheter 10 can include an elongate body 12 that includes at least a first lumen 22 extending between an inlet port 24 and an outlet port 26, and a second lumen 224 extending between a second inlet port 230 and a second outlet port 234 in elongate body 12. In the embodiment shown in FIG. 12, first expandable balloon 14 is shown in at least a partially deployed position and second expandable balloon 220 is in an undeployed state. As described herein, catheter 10 in FIG. 12 also includes a stent 240 positioned on catheter 10.

Medical catheter 10 also includes filter assembly 16 having expandable filter 36 positioned over at least a portion of first expandable balloon 14. As described herein, expandable filter 36 includes first portion 40 coupled to elongate body 12. Expandable filter 36 can also include second portion 42. In the present embodiment, second portion 42 of the expandable filter can be positioned around at least a portion of first expandable balloon 14 to form a second channel 450 between expandable filter 36 of filter assembly 16 and first expandable balloon 14.

In the present embodiment, second channel 450 can be formed between an inner surface 454 of expandable filter 36 and an outer surface 458 of first expandable balloon 14. As shown in FIG. 12, outer surface 458 of first expandable balloon 14 includes concave regions 460 and convex regions 464, where the area defined by concave regions 460, convex regions 464 and expandable filter 36 form second channel 450. Other configurations for outer surface 458 of first expandable balloon 14 are also possible, including but not limited to, those having a bifoil, trefoil, quatrefoil, or other configurations are possible.

In the present embodiment, there are shown a plurality of second channels 450 formed between expandable filter 36 of filter assembly 16 and first expandable balloon 14. Each of second channels 450 allows for fluid to be filtered to flow through filter assembly 16. In addition, first expandable balloon 14 in FIG. 12 is shown having a conical body shape from second portion 42 to distal end of balloon 32. This allows for additional filter material to be exposed to the fluid when filter assembly 16 is in operation. It is understood however, that first expandable balloon 14 can have any number of shapes (e.g., tubular) as described herein. In addition, expandable filter 36 can also include any number of shapes as described herein.

In one embodiment, second portion 42 of expandable filter 36 can be in direct contact with at least a portion of outer surface 458 of first expandable balloon 14. In one example, second portion 42 of expandable filter 36 include an elastic element that encircles at least a portion of first expandable balloon 14. The elastic element included in second portion 42 stretches as first expandable balloon 14 expands. In addition, the elastic element also provides a contractile force to lower expandable filter 36 when first expandable balloon 14 is deflated. In one embodiment, the elastic element of second portion 42 provides sufficient contractile force around first expandable balloon 14 to prevent second portion 42 of expandable filter 36 from moving longitudinally along first expandable balloon 14 when first expandable balloon 14 is in its inflated, deflated or intermediate state.

The elastic element present in the second portion of expandable filter 36 can be constructed from any number of materials. For example, the elastic element could be constructed of rubber, urethanes, nylons, silicones, polyesters, or other known elastic materials.

Medical device catheter 10 of the present invention can also have additional functional embodiments. For example, catheter 10 can be an "over the wire" endovascular device such as stent-deployment catheters and angioplasty catheters, as described herein. Alternatively, catheter 10 can be configured as an atherectomy catheter, an endovascular imaging device, a pressure monitor, an electrophysiology catheter, and an aspirator, which are adapted to receive guidewire 21. In addition, catheters 10 can include not only the full "over the wire" configuration, but also a rapid exchange, or partial over the wire, configuration as known in the art.

As described herein, the present invention provides a filtration device for use with vascular devices, such as balloon catheters. For example, the medical catheter of the present invention can be temporarily placed and used in either the venous portion or the aterial portion of the vasculature. In use, the medical catheter of the present invention can be used to filter and capture for removal from the vasculature pulmonary embolism due to, for example, hip surgery, major trauma, major abdominal or pelvic surgery, or immobilization. In addition, the medical catheter of the present invention can be used to filter and capture of an arterial embolism due to, for example, an angioplasty procedure with or without stent deployment and/or an atherectomy procedure.

The method of using the medical catheter of the present invention can include introducing medical device catheter 10 into a vas. The vas can include a duct or canal for conveying liquid, such as blood. An example of the vas includes, but is not limited to, blood vessels of both the arterial and ventricular circulatory system. Medical device catheter 10 can include any of the examples described herein.

Methods for introducing medical device catheters, such as those of the present invention, into arterial and/or venous blood vessels are known. Briefly, distal end of guidewire 21 can be passed through an occluding lesion, typically an atheromatous plaque, and positioned distal to the occlusion. Medical device catheter 10 of the present invention can then be inserted into the vessel over the over the proximal end of guidewire 21, and advanced distally until filter assembly 16 is positioned distal to the occluding lesion. First expandable balloon 14 can then be inflated to expand filter assembly 16. In one embodiment, first expandable balloon 14 can also dilate the lesion in the lumen of blood vessel. Alternatively, medical device catheter 10 can include a second expandable balloon 220 that can be positioned adjacent the lesion with filter assembly 16 is positioned distal to the occluding lesion. Expanded filter assembly 16 then filters fluid (e.g., blood) within the blood vessel to at least capture embolic particles, such as calcium, thrombi, plaque, and/or tissue debris.

Once the dilation of the lesion is completed, the expandable filter can then be drawn over and into contact with at least a portion of the first expandable balloon, as described herein. The medical device catheter, including the captured embolic material generated during the procedure, can then be withdrawn from the vessel after completion of the procedure.

First expandable balloon 16 or second expandable balloon 220 of medical device catheter 10 of the present invention can be used in deploying a stent, as discussed herein. In addition, filter assembly 16 can be used to release one or more drugs into the vas. For example, filter assembly 16 can be coated with drugs as described herein.

The present invention also provides for a method of making medical device catheter 10 of the present invention. In one embodiment, the method includes providing elongate body 12, as described herein, to which is coupled first expandable balloon 14, as described herein. Filter assembly 16 can then be provided to make medical device catheter 10, as described herein.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A medical catheter, comprising:
   an elongate body comprising at least a first lumen extending between an inlet port and an outlet port in the elongate body;
   a filter assembly comprising an expandable filter and a plurality of struts, the expandable filter comprising a proximal portion and a distal portion and each strut comprising a proximal end and a distal end, wherein the distal portion of the expandable filter is coupled to a portion of the medical catheter, the proximal ends of the struts are coupled to the elongate body, and the proximal portion of the expandable filter is coupled to the distal ends of the plurality of struts;
   a first expandable balloon comprising a proximal end and a distal end, wherein the proximal end and the distal end are coupled to the elongate body and the first expandable balloon is positioned so that, when inflated, at least a portion of the first expandable balloon contacts the proximal portion of the expandable filter, and wherein the outlet port is positioned between the proximal end and the distal end so as to be in fluid communication with the first expandable balloon; and
   a vascular stent positioned over at least a portion of the first expandable balloon.

2. The medical catheter of claim 1 wherein the distal portion of the expandable filter is coupled to the elongate body.

3. The medical catheter of claim 1 wherein the distal portion of the expandable filter is coupled to a portion of the first expandable balloon.

4. The medical catheter of claim 1 wherein the expandable filter is positioned over at least a portion of both the elongate body and the distal end of the first expandable balloon.

5. The medical catheter of claim 1 wherein the proximal portion of the expandable filter comprises a lip defining an opening into a volume defined by the expandable filter.

6. The medical catheter of claim 5 wherein the lip of the expandable filter comprises a predetermined shape.

7. The medical catheter of claim 6 wherein the predetermined shape is circular.

8. The medical catheter of claim 6 wherein the lip of the expandable filter comprises a diameter no larger than about a diameter of the first expandable balloon.

9. The medical catheter of claim 5 wherein the lip moves along an outer surface of the first expandable balloon as the first expandable balloon inflates to deploy the expandable filter.

10. The medical catheter of claim 5 wherein the proximal portion of the expandable filter to which the distal ends of the plurality of struts are coupled comprises the lip.

11. The medical catheter of claim 1 wherein the plurality of struts are unattached to the first expandable balloon.

12. The medical catheter of claim 1 further comprising a collar positioned around the elongate body adjacent the proximal end of the first expandable balloon, wherein the plurality of struts are coupled to the collar and wherein the collar further comprises a retracting mechanism to move the collar longitudinally along the elongate body and close the expandable filter over at least a portion of the first expandable balloon.

13. The medical catheter of claim 1 wherein the elongate body comprises a second lumen extending from a proximal end of the elongate body to a plurality of surfaces defining openings through the elongate body adjacent the proximal end of the first expandable balloon, wherein the plurality of struts are coupled to a retracting wire in the second lumen through the plurality of surfaces defining the openings, wherein the retracting wire moves to pull the plurality of struts longitudinally along the elongate body so as to draw the expandable filter over and into contact with at least a portion of the first expandable balloon.

14. The medical catheter of claim 1 wherein the struts comprise cables.

15. The medical catheter of claim 1 wherein the struts comprise a mesh.

16. The medical catheter of claim 1 wherein the struts comprise wire.

17. The medical catheter of claim 1 further comprising radial support arms coupled to the proximal portion and the distal portion of the expandable filter, wherein the radial support arms provide a predetermined shape to the expandable filter.

18. The medical catheter of claim 1 wherein the vascular stent is further positioned over at least a portion of the filter assembly.

19. The medical catheter of claim 1 wherein the first lumen of the elongate body further comprises a second outlet port in the elongate body, and wherein the medical catheter further comprising a second expandable balloon coupled to the elongate body and spaced apart from the first expandable balloon, wherein the second outlet portion is in fluid communication with the second expandable balloon.

20. The medical catheter of claim 1 wherein the first expandable balloon is positioned so that, when fully inflated, at least a portion of the first expandable balloon contacts the proximal portion of the expandable filter.

21. A medical device system, comprising:
a catheter comprising:
an elongate body comprising at least a first lumen extending between an inlet port and an outlet port in the elongate body;
a filter assembly comprising an expandable filter and a plurality of struts, the expandable filter comprising a proximal portion and a distal portion and each strut comprising a proximal end and a distal end, wherein the distal portion of the expandable filter is coupled to a portion of the medical catheter, the proximal ends of the struts are coupled to the elongate body, and the proximal portion of the expandable filter is coupled to the distal ends of the plurality of struts;
a first expandable balloon comprising a proximal end and a distal end, wherein the proximal end and the distal end are coupled to the elongate body and the first expandable balloon is positioned so that, when inflated, at least a portion of the first expandable balloon contacts the proximal portion of the expandable filter, and wherein the outlet port is positioned between the proximal end and the distal end so as to be in fluid communication with the first expandable balloon;
a vascular stent positioned over at least a portion of the first expandable balloon; and
an inflation device comprising a fluid output port to couple to the inlet port of the first lumen, and a fluid pressure generator coupled to the fluid output port to deliver pressurized fluid through the fluid output port to the first expandable balloon.

22. The medical device system of claim 21 wherein the first expandable balloon is positioned so that, when fully inflated, at least a portion of the first expandable balloon contacts the proximal portion of the expandable filter.

23. A medical catheter, comprising:
an elongate body comprising at least a first lumen extending between an inlet port and an outlet port in the elongate body;
a first expandable balloon comprising a proximal end and a distal end, wherein the proximal end and the distal end are coupled to the elongate body, and wherein the outlet port is positioned between the proximal end and the distal end so as to be in fluid communication with the first expandable balloon;
a vascular stent positioned over at least a portion of the first expandable balloon; and
a filter assembly comprising an expandable filter and a plurality of struts, wherein the expandable filter comprises a proximal portion and a distal portion and each strut comprises a proximal end and a distal end, wherein the distal portion of the expandable filter is coupled to a portion of the medical catheter, the proximal ends of the struts are coupled to the elongate body, and the proximal portion of the expandable filter is coupled to the distal ends of the plurality of struts, and wherein the first expandable balloon is positioned so that, when inflated, at least a portion of the first expandable balloon contacts the proximal portion of the expandable filter and a portion of the expandable filter is positioned around at least a portion of the first expandable balloon to form, when the expandable filter is deployed, a channel between the filter assembly and the first expandable balloon when the first expandable balloon is at least partially deflated after having been inflated.

24. The medical catheter of claim 23 wherein the distal portion of the expandable filter is coupled to the elongate body.

25. The medical catheter of claim 23 wherein the distal portion of the expandable filter is coupled to a portion of the first expandable balloon.

26. The medical catheter of claim 23 wherein the first expandable balloon comprises an outer surface and the expandable filter comprises an inner surface, wherein the outer surface and the inner surface form the channel between the filter assembly and the first expandable balloon.

27. The medical catheter of claim 23 wherein the plurality of struts are unattached to the first expandable balloon.

28. The medical catheter of claim 23 further comprising a collar positioned around the elongate body adjacent the proximal end of the first expandable balloon, wherein the plurality of struts are coupled to the collar and wherein the collar further comprises a retracting mechanism to move the collar longitudinally along the elongate body and close the expandable filter over at least a portion of the first expandable balloon.

29. The medical catheter of claim 23 wherein the elongate body comprises a second lumen extending from a proximal end of the elongate body to a plurality of surfaces defining openings through the elongate body adjacent the proximal end of the first expandable balloon, wherein the plurality of struts are coupled to a retracting wire in the second lumen through the plurality of surfaces defining the openings, wherein the retracting wire moves to pull the plurality of struts longitudinally along the elongate body so as to draw the expandable filter over and into contact with at least a portion of the first expandable balloon.

30. The medical catheter of claim 23 wherein the struts comprise cables.

31. The medical catheter of claim 23 wherein the struts comprise a mesh.

32. The medical catheter of claim 23 wherein the struts comprise wire.

33. The medical catheter of claim 23 wherein the expandable filter is positioned over at least a portion of both the elongate body and the distal end of the first expandable balloon.

34. The medical catheter of claim 23 wherein the proximal portion of the expandable filter comprises a lip defining an opening into a volume of the channel formed by the expandable filter and the first expandable balloon.

35. The medical catheter of claim 34 wherein the lip of the expandable filter comprises a predetermined shape.

36. The medical catheter of claim 35 wherein the predetermined shape is circular.

37. The medical catheter of claim 35 wherein the lip of the expandable filter comprises a diameter no larger than about a diameter of the first expandable balloon.

38. The medical catheter of claim 34 wherein the lip moves along an outer surface of the first expandable balloon as the first expandable balloon inflates to deploy the expandable filter.

39. The medical catheter of claim 34 wherein the proximal portion of the expandable filter to which the distal ends of the plurality of struts are coupled comprises the lip.

40. The medical catheter of claim 23 further comprising radial support arms coupled to the distal portion and the proximal portion of the expandable filter, wherein the radial support arms provide a predetermined shape to the expandable filter.

41. The medical catheter of claim 23 wherein the vascular stent is positioned over at least a portion of the filter assembly and the first expandable balloon.

42. The medical catheter of claim 23 wherein the first lumen of the elongate body further comprises a second outlet port in the elongate body, and wherein the medical catheter further comprising a second expandable balloon coupled to the elongate body and spaced apart from the first expandable balloon, wherein the second outlet portion is in fluid communication with the second expandable balloon.

43. The medical catheter of claim 23 wherein the first expandable balloon is positioned so that, when fully inflated, at least a portion of the first expandable balloon contacts the proximal portion of the expandable filter.

44. A method, comprising:
introducing a medical device catheter into a vas, wherein the medical device catheter comprises:
an elongate body comprising at least a first lumen extending between an inlet port and an outlet port in the elongate body;
a filter assembly comprising an expandable filter and a plurality of struts, the expandable filter comprising a proximal portion and a distal portion and each strut comprising a proximal end and a distal end, wherein the distal portion of the expandable filter is coupled to a portion of the medical catheter, the proximal ends of the struts are coupled to the elongate body, and the proximal portion of the expandable filter is coupled to the distal ends of the plurality of struts;
a first expandable balloon comprising a proximal end and a distal end, wherein the proximal end and the distal end are coupled to the elongate body and the first expandable balloon is positioned so that, when inflated, at least a portion of the first expandable balloon contacts the proximal portion of the expandable filter, and wherein the outlet port is positioned between the proximal end and the distal end so as to be in fluid communication with the first expandable balloon; and
a vascular stent positioned over at least a portion of the first expandable balloon; and
inflating the expandable balloon to expand the filter assembly.

45. The method of claim 44 further comprising filtering fluid with the filter assembly within the vas.

46. The method of claim 44 wherein introducing the medical device into the vas comprises introducing the medical device into a blood vessel.

47. The method of claim 46 wherein inflating the expandable balloon dilates a lumen of the blood vessel.

48. The method of claim 47 further comprising capturing particles in blood with the filter assembly within the blood vessel.

49. The method of claim 44 wherein inflating the expandable balloon to expand the filter assembly comprises extending a portion of the expandable filter beyond the distal end of the expandable balloon.

50. The method of claim 44 further comprising deploying the stent when inflating the expandable balloon, and capturing particles with the expanded filter assembly.

51. The method of claim 44 further comprising releasing one or more drugs from the filter assembly into the vas.

52. The method of claim 44 wherein inflating the expandable balloon to expand the filter assembly to filter fluid inside the vas comprises capturing particles from the fluid in the filter assembly.

53. The method of claim 44 further comprising drawing the expandable filter over and into contact with at least a portion of the first expandable balloon.

54. A method, comprising:
introducing a medical device catheter into a blood vessel, wherein blood moves through the blood vessel, wherein the medical device catheter comprises:
an elongate body comprising at least a first lumen extending between an inlet port and an outlet port in the elongate body;
a filter assembly comprising an expandable filter and a plurality of struts, the expandable filter comprising a proximal portion and a distal portion and each strut comprising a proximal end and a distal end, wherein the distal portion of the expandable filter is coupled to a portion of the medical catheter, the proximal ends of the struts are coupled to the elongate body, and the proximal portion of the expandable filter is coupled to the distal ends of the plurality of struts;
a first expandable balloon comprising a proximal end and a distal end, wherein the proximal end and the distal end are coupled to the elongate body and the first expandable balloon is positioned so that, when inflated, at least a portion of the first expandable balloon contacts the proximal portion of the expandable filter, and wherein the outlet port is positioned between the proximal end and the distal end so as to be in fluid communication with the first expandable balloon; and
a vascular stent positioned over at least a portion of the first expandable balloon;
inflating the expandable balloon in the blood vessel deploying the filter assembly;
at least partially deflating the expandable balloon to form a channel between the filter assembly and the expandable balloon through which the blood moves; and
capturing particles from the blood in the filter assembly moving through the channel.

55. A method of making a medical device catheter, comprising:
providing an elongate body comprising at least a first lumen extending between an inlet port and an outlet port in the elongate body;
coupling a first expandable balloon comprising a proximal end and a distal end to the elongate body, wherein the proximal end and the distal end are coupled to the elongate body, and wherein the outlet port is positioned between the proximal end and the distal end so as to be in fluid communication with the first expandable balloon;
providing a vascular stent positioned over at least a portion of the first expandable balloon; and
providing a filter assembly comprising an expandable filter and a plurality of struts, wherein the expandable filter comprises a proximal portion and a distal portion and each strut comprises a proximal end and a distal end, wherein the distal portion of the expandable filter is coupled to a portion of the medical catheter, the proximal ends of the struts are coupled to the elongate body, and the proximal end of the expandable filter is coupled to the distal ends of the plurality of struts, and wherein the first expandable balloon is positioned so that, when inflated, at least a portion of the first expandable balloon contacts the proximal portion of the expandable filter and a portion of the expandable filter is positioned around at least a portion of the first expandable balloon to form, when the expandable filter is deployed, a channel between the filter assembly and the first expandable balloon when the first expandable balloon is at least partially deflated after having been inflated.

56. A medical device system, comprising:
a catheter comprising:
  an elongate body comprising at least a first lumen extending between an inlet port and an outlet port in the elongate body;
  a first expandable balloon comprising a proximal end and a distal end, wherein the proximal end and the distal end are coupled to the elongate body, and wherein the outlet port is positioned between the proximal end and the distal end so as to be in fluid communication with the first expandable balloon;
  a vascular stent positioned over at least a portion of the first expandable balloon; and
  a filter assembly comprising an expandable filter and a plurality of struts, wherein the expandable filter comprises a proximal portion and a distal portion and each strut comprises a proximal end and a distal end, wherein the distal portion of the expandable filter is coupled to a portion of the medical catheter, the proximal ends of the struts are coupled to the elongate body, and the proximal end of the expandable filter is coupled to the distal ends of the plurality of struts, and wherein the first expandable balloon is positioned so that, when inflated, at least a portion of the first expandable balloon contacts the proximal portion of the expandable filter and a portion of the expandable filter is positioned around at least a portion of the first expandable balloon to form, when the expandable filter is deployed, a channel between the filter assembly and the first expandable balloon when the first expandable balloon is at least partially deflated after having been inflated; and
  an inflation device comprising a fluid output port to couple to the inlet port of the first lumen, and a fluid pressure generator coupled to the fluid output port to deliver pressurized fluid through the fluid output port to the first expandable balloon.

57. The medical device system of claim 56 wherein the first expandable balloon is positioned so that, when fully inflated, at least a portion of the first expandable balloon contacts the proximal portion of the expandable filter.

* * * * *